US012235913B2

(12) United States Patent
Vittorio

(10) Patent No.: US 12,235,913 B2
(45) Date of Patent: *Feb. 25, 2025

(54) CONTENT SEARCH AND RESULTS

(71) Applicant: Steven Michael Vittorio, San Francisco, CA (US)

(72) Inventor: Steven Michael Vittorio, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/452,955

(22) Filed: Oct. 29, 2021

(65) Prior Publication Data

US 2022/0050882 A1 Feb. 17, 2022

Related U.S. Application Data

(63) Continuation of application No. 15/030,817, filed as application No. PCT/US2014/061806 on Oct. 22, 2014, now Pat. No. 11,222,084, which is a continuation-in-part of application No. 14/521,110, filed on Oct. 22, 2014, now Pat. No. 11,238,114, and (Continued)

(51) Int. Cl.
| | |
|---|---|
| *G06F 16/9535* | (2019.01) |
| *G06F 16/2457* | (2019.01) |
| *G09B 5/02* | (2006.01) |
| *G09B 5/04* | (2006.01) |
| *G09B 5/06* | (2006.01) |
| *G16H 70/60* | (2018.01) |

(52) U.S. Cl.
CPC .... *G06F 16/9535* (2019.01); *G06F 16/24578* (2019.01); *G16H 70/60* (2018.01); *G09B 5/02* (2013.01); *G09B 5/04* (2013.01); *G09B 5/065* (2013.01)

(58) Field of Classification Search
CPC .................................................. G06F 3/0488
USPC ............................................................ 434/322
See application file for complete search history.

(56) References Cited

U.S. PATENT DOCUMENTS

| | | |
|---|---|---|
| 6,626,959 B1 | 9/2003 | Moise et al. |
| 6,987,945 B2 | 1/2006 | Corn et al. |

(Continued)

FOREIGN PATENT DOCUMENTS

WO 2014/071033 A1 5/2014

OTHER PUBLICATIONS

International Search Report in International Application No. PCT/US2014/061806, filed Oct. 22, 2014.

(Continued)

*Primary Examiner* — Xuan M Thai
*Assistant Examiner* — Sadaruz Zaman
(74) *Attorney, Agent, or Firm* — SALIWANCHIK, LLOYD & EISENSCHENK

(57) ABSTRACT

A search request for content can be initiated by a user, and the content that is relevant to the search request can be identified and presented in a manner that indicates the content's trustworthiness or relevancy. The identified content can be ranked based on the number of times the content has been referenced as well as by source that referenced the content. The relevant identified content can then be displayed in an ordered list that is ordered based on the number of times the content has been referenced. In some cases, the order may be modified by the authority of the source.

43 Claims, 11 Drawing Sheets

Related U.S. Application Data a continuation-in-part of application No. 14/521,149, filed on Oct. 22, 2014, now Pat. No. 10,275,531.

(60) Provisional application No. 61/894,378, filed on Oct. 22, 2013, provisional application No. 61/979,555, filed on Apr. 15, 2014.

(56) References Cited

U.S. PATENT DOCUMENTS

| | | | |
|---|---|---|---|
| 7,502,836 B1* | 3/2009 | Menditto | H04L 67/568 |
| | | | 709/217 |
| 7,526,475 B1 | 4/2009 | Verstak et al. | |
| 7,650,597 B2* | 1/2010 | Bohlmann | G06F 40/151 |
| | | | 717/136 |
| 8,001,141 B1 | 8/2011 | Bar | |
| 8,090,717 B1 | 1/2012 | Bharat et al. | |
| 8,352,467 B1 | 1/2013 | Guha | |
| 8,392,244 B1 | 3/2013 | O'Halloran | |
| 8,417,698 B2* | 4/2013 | Yoo | G06Q 30/02 |
| | | | 707/732 |
| 8,616,895 B2 | 12/2013 | Brown | |
| 8,676,828 B1* | 3/2014 | Agarwal | G06F 16/3322 |
| | | | 706/14 |
| 8,725,768 B2* | 5/2014 | Jones | G06F 16/335 |
| | | | 707/781 |
| 8,805,814 B2 | 8/2014 | Zijlstra et al. | |
| 8,874,465 B1* | 10/2014 | Heiser, III | G06Q 30/0215 |
| | | | 705/14.1 |
| 8,875,038 B2* | 10/2014 | Ismalon | H04L 67/1095 |
| | | | 715/708 |
| 8,938,438 B2* | 1/2015 | Nijjer | G06F 16/9535 |
| | | | 707/750 |
| 8,954,420 B1 | 2/2015 | Khan et al. | |
| 8,965,873 B2* | 2/2015 | Khan | G06F 16/951 |
| | | | 707/706 |
| 8,972,391 B1 | 3/2015 | McDonnell et al. | |
| 9,330,183 B2* | 5/2016 | Woss | G06F 16/9535 |
| 9,361,363 B2* | 6/2016 | Whitnah | G06Q 50/01 |
| 9,367,625 B2* | 6/2016 | Raina | G06F 16/9535 |
| 9,367,880 B2* | 6/2016 | Raina | G06F 16/24578 |
| 9,514,230 B2* | 12/2016 | Raina | G06F 16/24539 |
| 10,162,900 B1 | 12/2018 | Chatterjee et al. | |
| 10,275,531 B2 | 4/2019 | Vittorio | |
| 10,726,083 B2* | 7/2020 | Annau | G06F 16/9538 |
| 10,885,552 B2* | 1/2021 | Heiser, II | G06Q 30/02 |
| 11,531,678 B2* | 12/2022 | Liu | G06F 16/9535 |
| 2002/0078045 A1 | 6/2002 | Dutta | |
| 2002/0161757 A1 | 10/2002 | Mock et al. | |
| 2003/0040976 A1 | 2/2003 | Adler et al. | |
| 2003/0125983 A1 | 7/2003 | Flack et al. | |
| 2003/0130994 A1* | 7/2003 | Singh | G06F 16/93 |
| 2003/0144877 A1 | 7/2003 | Goldmann et al. | |
| 2003/0163375 A1* | 8/2003 | Dombrowski | G06Q 30/0276 |
| | | | 705/14.72 |
| 2004/0153343 A1 | 8/2004 | Gotlib et al. | |
| 2004/0162772 A1 | 8/2004 | Lewis | |
| 2005/0026131 A1 | 2/2005 | Elzinga et al. | |
| 2005/0060312 A1* | 3/2005 | Curtiss | G06F 16/24578 |
| 2005/0065959 A1 | 3/2005 | Smith et al. | |
| 2005/0079477 A1* | 4/2005 | Diesel | H04L 67/01 |
| | | | 434/350 |
| 2005/0228593 A1 | 10/2005 | Jones | |
| 2006/0112085 A1 | 5/2006 | Zijlstra et al. | |
| 2007/0185864 A1 | 8/2007 | Budzik et al. | |
| 2007/0208751 A1* | 9/2007 | Cowan | G06Q 30/02 |
| 2007/0255805 A1 | 11/2007 | Beams et al. | |
| 2008/0046286 A1 | 2/2008 | Halsted | |
| 2008/0208624 A1 | 8/2008 | Morita et al. | |
| 2008/0222142 A1* | 9/2008 | O'Donnell | G06F 16/24578 |
| | | | 707/999.005 |
| 2008/0270451 A1 | 10/2008 | Thomsen et al. | |
| 2009/0106799 A1 | 4/2009 | Park et al. | |
| 2009/0138371 A1 | 5/2009 | McGee | |
| 2009/0142742 A1* | 6/2009 | Goldberg | G09B 7/02 |
| | | | 434/362 |
| 2009/0182725 A1 | 7/2009 | Govani et al. | |
| 2009/0271379 A1 | 10/2009 | Bakalash et al. | |
| 2009/0281988 A1 | 11/2009 | Yoo | |
| 2010/0179828 A1 | 7/2010 | Kelly et al. | |
| 2010/0211564 A1 | 8/2010 | Cohen et al. | |
| 2010/0268552 A1 | 10/2010 | Schoenberg et al. | |
| 2010/0286993 A1 | 11/2010 | Lovelace | |
| 2011/0004588 A1 | 1/2011 | Leitersdorf et al. | |
| 2011/0010366 A1 | 1/2011 | Varshavshy et al. | |
| 2011/0055189 A1 | 3/2011 | Effrat et al. | |
| 2011/0144908 A1 | 6/2011 | Cheong | |
| 2011/0173225 A1 | 7/2011 | Stahl et al. | |
| 2011/0212430 A1 | 9/2011 | Smithmier et al. | |
| 2011/0246468 A1 | 10/2011 | Raines | |
| 2012/0005201 A1 | 1/2012 | Ebanks | |
| 2012/0066167 A1 | 3/2012 | Fokoue et al. | |
| 2012/0066256 A1 | 3/2012 | Ramamurthi et al. | |
| 2012/0117088 A1 | 5/2012 | Kawakami et al. | |
| 2012/0129139 A1 | 5/2012 | Partovi | |
| 2012/0221442 A1 | 8/2012 | Olejniczak et al. | |
| 2012/0245952 A1 | 9/2012 | Halterman et al. | |
| 2012/0251993 A1 | 10/2012 | Chidambaran et al. | |
| 2013/0040275 A1 | 2/2013 | Gowda | |
| 2013/0095464 A1* | 4/2013 | Ediger | G09B 5/125 |
| | | | 434/322 |
| 2013/0097144 A1 | 4/2013 | Siamwalla et al. | |
| 2013/0173639 A1 | 7/2013 | Chandra et al. | |
| 2013/0262142 A1 | 10/2013 | Sethumadhavan et al. | |
| 2013/0280682 A1 | 10/2013 | Levine et al. | |
| 2014/0006930 A1 | 1/2014 | Hollis et al. | |
| 2014/0058753 A1 | 2/2014 | Wild | |
| 2014/0108369 A1 | 4/2014 | Nijer | |
| 2014/0122456 A1 | 5/2014 | Dies | |
| 2014/0143232 A1 | 5/2014 | Abe | |
| 2015/0111190 A1 | 4/2015 | Vittorio | |
| 2015/0154646 A1 | 6/2015 | Mishra et al. | |
| 2015/0187228 A1 | 7/2015 | Boguski et al. | |
| 2015/0248484 A1 | 9/2015 | Yu et al. | |
| 2016/0111021 A1 | 4/2016 | Knoche et al. | |
| 2016/0259858 A1 | 9/2016 | Vittorio | |
| 2018/0137125 A1* | 5/2018 | Vittorio | G06F 16/2477 |
| 2019/0068659 A1 | 2/2019 | Davar et al. | |
| 2019/0325016 A1 | 10/2019 | Nicholson et al. | |

OTHER PUBLICATIONS

Office Action dated Nov. 2, 2017 in U.S. Appl. No. 14/521,149.
International Search Report in International Application No. PCT/US2016/028080, filed Apr. 18, 2016.
Office Action dated Nov. 18, 2019 in U.S. Appl. No. 15/030,817.
Notice of Allowance dated Oct. 4, 2021 in U.S. Appl. No. 15/566,977.
Notice of Allowance dated Dec. 18, 2018 in U.S. Appl. No. 14/521,149.
Office Action dated Jan. 1, 2021 in U.S. Appl. No. 15/566,977.
Office Action dated Apr. 27, 2018 in U.S. Appl. No. 14/521,149.
Office Action dated Sep. 4, 2020 in U.S. Appl. No. 15/030,817.
Office Action dated Apr. 6, 2020 in U.S. Appl. No. 15/566,977.
Notice of Allowance dated Sep. 3, 2021 in U.S. Appl. No. 15/030,817.
Notice of Allowance dated Sep. 17, 2021 in U.S. Appl. No. 14/521,110.
Office Action dated Jan. 10, 2020 in U.S. Appl. No. 14/521,110.
Office Action dated Sep. 4, 2020 in U.S. Appl. No. 14/521,110.
Advisory Action dated Mar. 24, 2020 in U.S. Appl. No. 14/521,110.
Office Action dated Jul. 15, 2021 in U.S. Appl. No. 14/521,110.
Office Action dated Sep. 26, 2016 in U.S. Appl. No. 14/521,110.
Advisory Action dated Feb. 25, 2020 in U.S. Appl. No. 15/030,817.
Office Action dated Jul. 14, 2021 in U.S. Appl. No. 15/030,817.
Office Action dated Oct. 14, 2016 in U.S. Appl. No. 15/030,817.
Office Action dated Apr. 12, 2017 in U.S. Appl. No. 14/521,149.
Notice of Allowance dated Feb. 24, 2023 in U.S. Appl. No. 17/452,960.

* cited by examiner

CONTENT SEARCH AND RESULTS

CROSS-REFERENCE TO RELATED APPLICATIONS

This application is a continuation of U.S. application Ser. No. 15/030,817, filed Apr. 20, 2016; which is the U.S. national stage application of International Patent Application No. PCT/US2014/061806, filed Oct. 22, 2014, which is a continuation in part of U.S. application Ser. No. 14/521,110, filed Oct. 22, 2014, and U.S. application Ser. No. 14/521,149, filed Oct. 22, 2014, now U.S. Pat. No. 10,275,531, issued Apr. 30, 2019, both of which claim the priority benefit of U.S. Provisional Application Ser. No. 61/894,378, filed Oct. 22, 2013, and U.S. Provisional Application Ser. No. 61/979,555, filed Apr. 15, 2014, all of which are incorporated herein by reference in their entirety.

BACKGROUND

Searching for certain kinds of content over the Internet can be difficult because it is not easy to determine whether the content is the most appropriate for the task and topic at hand. Although there are a number of websites that sell or lend textbooks, educational content, and medical content, a search of this content is generally conducted directly using key terms input to a search bar.

Unfortunately, it is not always possible to determine which of a number of results would be the most likely one to be helpful in understanding a subject. Sometimes results are ranked according to relevancy, but the relevancy ranking may only be a function of a number of times a term is found in the text of a web page, or may be at least partly based off of user reviews, rankings, or responses. If the results are provided alphabetically, then there is no way to know which is the best content for a particular situation. In some cases, there may be reviews of the content, which can help inform the decision. However, the trustworthiness of the suggestion or review may be difficult to determine.

BRIEF SUMMARY

Systems and techniques for facilitating content search and results are described. The content can be presented in a manner that indicates the content's trustworthiness or relevancy.

Example embodiments are described in which systems and techniques are illustrated in respect to several content categories, including educational content and medical content. An example embodiment is also described in which multiple content types relating to a search query may be shown in relation to one another.

A method of facilitating content search and results can include, for example, identifying a plurality of content in response to receiving a search query, identifying a number of times each content of the plurality of content has been referenced by sources of a set of at least one designated source, and generating a search result of the plurality of content that is ordered based on the number of times each content has been referenced.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
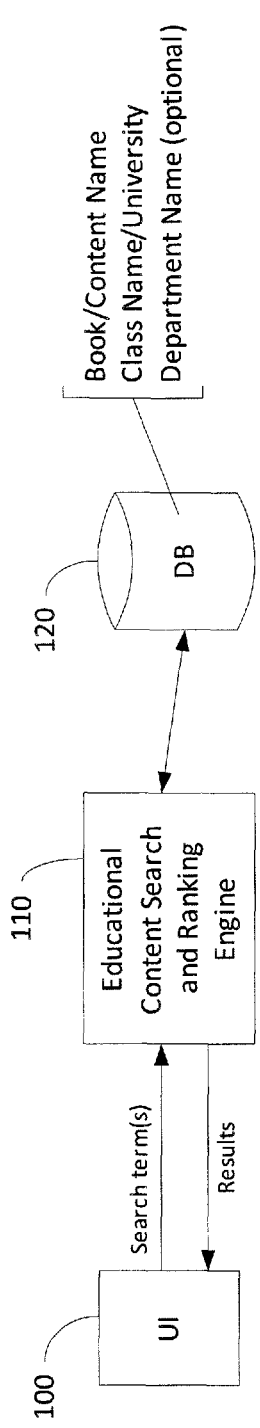
FIG. 1 illustrates an operating environment in which certain embodiments may be implemented.

Systems and techniques for facilitating content search and results are described. The content can be presented in a manner that indicates the content's trustworthiness or relevancy.

Example embodiments are described in which systems and techniques are illustrated in respect to several content categories, including educational content and medical content. An example embodiment is also described in which multiple content types relating to a search query may be shown in relation to one another.

Educational Content

In embodiments describing or pertinent to educational content, systems and techniques for facilitating educational content search and results are described. The educational content can be presented in a manner that indicates trustworthiness or relevancy based on an authoritative source—for example, a school or educational organization (private or government) or library. The content being referenced may include books, journal articles, website sources, course packet materials, video content, audio content, other multimedia content, software content, interactive demo content, transcriptions of spoken content into written content, and translations of content. It should be noted that, while books are frequently used as examples of educational content herein, techniques and systems are applicable to a wide variety of educational content.

The sources referencing the educational content can include universities and other formal educational institutions such as preschool, primary school (elementary), secondary school (middle, junior high, high, community college), tertiary school (non-compulsory, university, undergraduate, graduate, post graduate, vocational), vocational school, and specialty school. Alternative education organizations and systems including homeschooling and self-learning systems may also provide sources for educational content. Sources may also include libraries, such as school or university libraries, as well as other institutional libraries or research libraries.

A school or education organization may reference educational content by, for example, indicating particular content to be read, viewed, listened to or otherwise used as part of an assignment; providing required, recommended, optional or suggested reading, viewing, and/or listening; or even listing the content as being authored or edited by an employee of the school. A library may reference educational content by possessing one or more copies of the content in the library's collection.

The manner that an educational content is referenced may in some implementations affect how the educational content is ranked and/or counted. For example, certain materials may be indicated as required reading for a class (e.g., specific pages are assigned as homework) whereas other materials may be suggested as supplemental, optional or additional reading (not specifically required as part of the homework assignment). In some implementations all or a subset of referenced materials are included as part of the results. In some implementations, only the required reading materials are included as part of the results. In other implementations, only the supplemental, non-required materials are included as part of the results. In some implementations, the manner in which educational content is referenced is indicated as metadata associated with the particular content.

In some cases, a weight may be assigned to the content (for the rankings) based on the manner in which educational content is referenced. In some cases, no distinction based on the manner in which the content is referenced is made in the rankings. In other cases, "assigned" (e.g., required as part of an assignment) may be weighted over "recommended" (e.g., not required/optional supplemental to an assignment) content. In yet other cases, a distinction may be provided between assigned material and recommended material through use of an indicator in the search results. Accordingly, it should be understood that the content ranking may be based on the manner in which content is referenced by a source (e.g., whether the manner falls into a category such as required, recommended, optional, extra/supplemental, and/or mentioned reading); and when reference is made to "referenced" content any combination of content found in a syllabus (or curriculum plan or other listing) for a particular course (or general subject) may be included in all permutations.

In some implementations, only "recommended" content is presented for a user. In some implementations only "required" (specifically assigned) content is presented for a user. In some implementations, both the recommended and the required content are presented to the user. In some implementations where both the recommended and the required content are presented to the user, the system may be agnostic about the manner in which the content is referenced and may present results in a manner as if there is no difference between content that is recommended and content that is required. In some implementations where both the recommended and the required content are presented to the user, the manner in which the content is referenced may not affect how the content is ranked, but can be indicated to the user so that the user knows whether the content was a required content and/or recommended content by a particular source. One manner of indicating the manner in which the content was referenced is to include a particular icon or indication in association with the indicator of the class, school, or other level of granularity relevant to the source that referenced the content. In some cases, faces of teachers/ professors may be used.

In some implementations where both the recommended and the required content are presented to the user, the manner in which the content is referenced can affect the rankings. For example, each "required" reference to a piece of content may be weighted differently than each "recommended" reference to that piece of content. As another example, the number of required references to a piece of content may be used as a tie-breaker when two pieces of content have a same number of total references, but differing numbers of required references (e.g., both pieces of content have 10 references, but one was referenced as required 7 times and the other was indicated as required only 6 times— the remaining references being recommendations).

In some implementations, sections within referenced content can be ranked, where the referenced portions of each educational content result can be presented.

The information about educational content referenced by a school (or education organization) may be gathered from sources including, but not limited to, schools, professors, teachers, libraries, course syllabi, school websites, faculty, book stores (online and brick-and-mortar), library holdings catalogs, and even students (who relay the assignments, required, and recommended materials given by their school).

FIG. 1 illustrates an operating environment in which embodiments may be implemented. Referring to FIG. 1, a user may conduct a search of educational content through a user interface (UI) 100. The search can be conducted on, for example, course titles, titles of content (e.g., book titles), text within the content, school (including department or school within a school) and/or library, degree/major title, or a combination of one or more of these categories. The areas for the search may be specified by the educational content search and ranking engine 110 (e.g., via a drop-down menu) or may include free-form input provided by the user via the user interface 100 (e.g., via a search bar).

Figure 2:
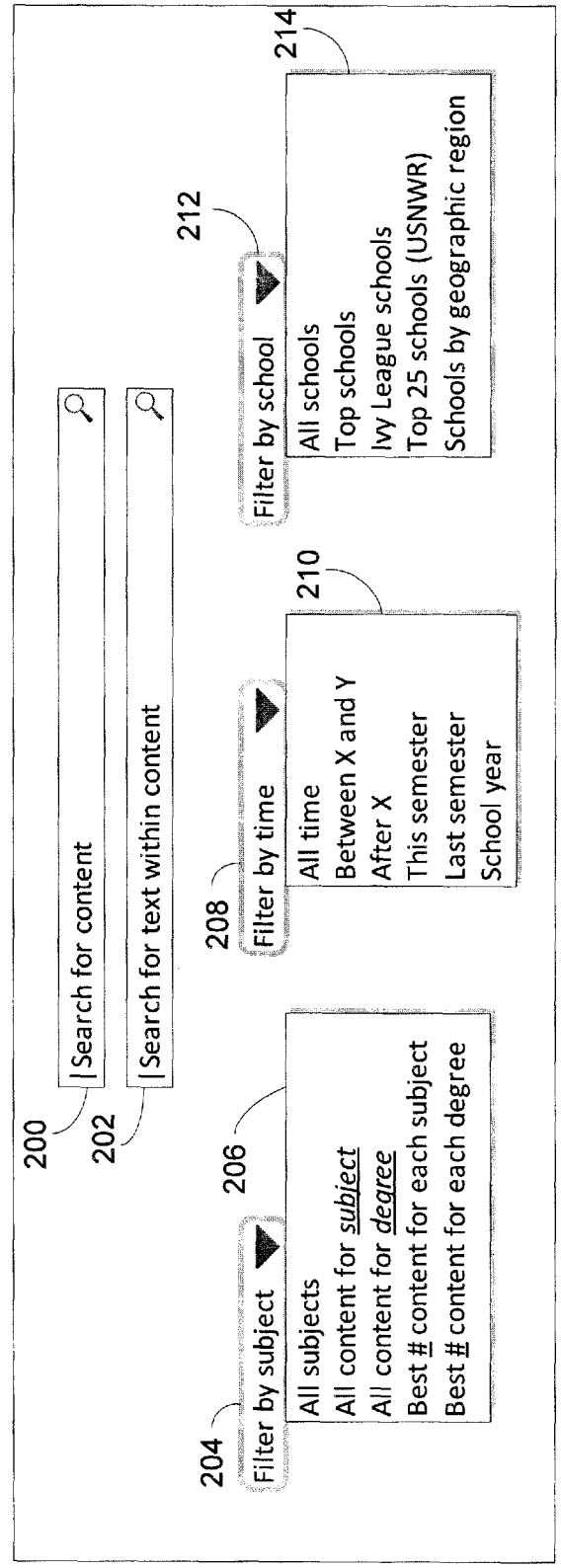
FIG. 2 illustrates an example user interface of a search page for educational content.

The user interface may include features as illustrated in FIG. 2. As shown in FIG. 2, a first input field 200 can be provided for receiving a search query for content. In some cases, a second search field 202 may be provided for searching for text within content. The search fields may be separate input fields or a single input field for conducting one or both searches. The search query may be refined by using one or more filters.

In some embodiments, when a search is conducted for text within content, the results can surface matching search terms as well as context for the matching search terms. For example, 80 words in front of and 80 words following a matching term in a piece of content can be displayed as part of the result for searching text within content. In some cases, the portions of the content that are shown first can be based on the amount of discussion related to the search query. For example, a matching word in a list may be given less prominence than sections of text containing substantive discussion related to the query. Also for example, a preview that would feature more matches of the search term(s) would be ranked above a preview that would contain fewer, and this may be a tie breaker for within content ranked previews.

In some embodiments, when a search is conducted for term(s) within content, the results can surface content (and corresponding previews when used) that contain a matching (or related) term both within the content and in meta-content, such as the prefix, index, glossary, summary, and table of contents. In some embodiments, only the pages listed from a specific table of contents, prefix, summary, or index match may be shown. In some embodiments, matches for content contained in the prefix, summary, index, glossary, or table of contents may be excluded from the search results. In some embodiments, content related to the search terms may be required to be in the content and within the index, glossary, or table of contents, which may minimize the return of results that mention a term but do not relate to the appropriate topic/concept/subject. In some implementations, any matching content may be returned. Any and all content matching options may be user-selectable.

Users do not need to do a search to access the content as the content may be listed in a default or otherwise optimized manner before a specific search is entered by the user. In some implementations, an ordered listing of content can be presented on a landing page (e.g., "home page") of an educational content listing website rendered in a user's browser application (and providing a user interface to the educational content search and ranking engine). The default ordered listing may be of content for all the schools (as known from the database or other structured data stored on a resource for the educational content search and ranking engine).

For example, the schools included in "all the schools" may be through school ranking systems such as the U.S. News and World Report Best Education rankings (e.g., Best Colleges, Best Graduate Schools, Best Online Programs, Best High Schools, and the like). The home page may then show all the educational content for the top number of schools indicated by the ranking system in an ordered list of content according to the number of times that content is referenced by those schools (where, for example, each item of content is counted only once per school even where multiple courses at that school may reference the content). Specific tie-breakers may be applied to determine the order of the content when more than one item of content is referenced the same number of times. User-adjustable filters may be used to narrow the results before a search is conducted or after the search is conducted. Educational content may be, for example, books, videos, audios, and articles.

A "filter by subject" 204 can provide filtering options 206 such as, but not limited to, enabling a search of content for all subjects, all content for a specified subject, all content for a specified degree and/or major, a designated number of content for each subject (e.g., "top 10 psychology books") and a number of content for each degree (e.g., "top 25 books for a degree in civil engineering") as some examples. Filtering by one or more topics may also be accomplished.

A "filter by time" 208 can provide filtering options 210 such as, but not limited to, enabling a search of content referenced at any time, between certain dates, after a certain date, for a certain year, for a certain school year, for the present semester, for a previous semester, and a designated one or more semesters as some examples.

A "filter by school" 212 can provide filtering options 214 such as, but not limited to, enabling a search of content for one, multiple, or all schools, for designated schools such as top schools, for Ivy League schools, for the top 25 (or other "top" number) schools according to the U.S. News and World Report rankings or other rankings, and schools by geographic region as some examples.

Other filter types are also possible. For example, searches may be filtered according to educational source in other ways, including but not limited to, magnet (and or charter) programs or schools, school districts, specialized schools, school board, school zone, and grade levels. Additional filter categories may be added to further filter results by type/kind/category of content, e.g., book, article, video, audio recording, multimedia contents, interactive demo, and training software.

In some embodiments, available filter options may be determined or dynamically redefined by prior filter selections, as for example when selection of a "degree" filter surfaces an additional filter based on different degree names. Sub-filters may, for example, further refine broader content types (e.g., novel and textbook as sub-types of book) or language (e.g. English, Spanish), or original language.

Of course other designations may be provided and even natural language queries may be used in certain implementations. The manner and menu for applying the filter(s) may be any suitable tool bar, input field or menu for providing the information.

A degree, class schedule, or interest search may be carried out through the described search and ranking engine via a content search 200. For example, in response to receiving a request for content directed to a degree program (set using filter element 204) and a time factor like a grade level (including continuing education) (set using filter element 208), the system can provide results of referenced content to cover the referenced content from the requested grade level (or age) through completion of the degree according to the available or selected educational sources.

In some implementations, a degree audit may be provided as a filter of the educational content. The degree audit search or filter may be used as an entry point to other searches, for example, each course for the degree can generate ordered listings of educational content. A keyword search may be used or a comparison of courses for degrees from a set of sources (e.g., a set of schools). The degree audit may incorporate class name filtering/search. For example, a degree audit may return content that school(s) reference for the particular class names corresponding to the degree. In some cases, the courses may include general education requirements as well as core curriculum. The results may be further filtered according to year (e.g., what the degree courses were for a particular year) and time-frame (e.g., from what grade level to what grade level). Searches may be conducted within the results in any manner such as described herein. In some cases, the exact course names for selected schools (from the selected schools degree audits) are used to generate the results for the degree audit search and/or filter. In some cases, key words are used to generate results for the various courses expected for a degree.

It should be understood that the degrees available for the degree audit may include primary or secondary school level programming or curriculum as well as or in addition to college and university level curriculum. In some cases, the degree audit can be based on published or official school curriculum. In some cases, the degree audit can be based on what students actually took to obtain their degree (or attain graduation to a next level). Electives and minors may be included. In yet other cases, a combination of official school curriculum and student-reported courses may be used.

Results of degree audits may include highlighting or other indications emphasizing particular content. For example, a top 10 content may be indicated covering a top content for each of 10 courses (or less courses and more content associated with the courses) so that a user may obtain a cohesive picture for the degree and possibly be inclined to view and/or purchase the content. As one example, a top 20 items for a law degree may be presented to the user; each item being a most referenced for a particular course. The highlighting may guide a user to specific subjects/topics/concepts within the general subject of law.

In some cases, results of a degree audit may be organized by specific degree or subject name or by a more general topic name (e.g., specific degree of tax law or more general topic of law; a specific degree of cognitive psychology or a more general topic of psychology).

Degree audits may include any of the filtering described herein (e.g., subject, time, school, within content). Filtering by school(s) can facilitate a comparison of degree/major audits across schools. Other filters may be available, including filtering by degree, which may use same named degrees across schools along with their respective degree audits with listed class names to search all listed class names and the degree name itself, in order to return a filtered ranked list by degree. In some cases, filtering by subject may filter by class name(s) (or major or major/degree) and may be used in place of or in addition to filtering by degree. A menu may be presented so a user can select a degree and then one or more subjects. It may also be possible to filter by teacher/professor or by ranking of teachers/professors (as indicated by review sites).

Returning to FIG. 1, search terms entered via the user interface 100 are used by an educational content search and ranking engine 110 to search a database (DB) 120. The database 120 can include structured information regarding educational content. A wide variety of educational content information may be stored, some of which may support the use of filtering categories described above. The database can be generated, for example, based on the books and other content referenced by universities. Elementary and secondary education may also provide syllabi (or other course or curriculum plans) that can be used to generate rankings.

The educational content search and ranking engine 110 can use the search terms provided via the user interface 110 to identify relevant educational content from the database 120. According to certain embodiments, the relevant educational content can initially be based on a search of content title (e.g., book name) and class name (e.g., for each university). In one such implementation, all books or other content titles that have matching terms in the class names are retrieved from the database and ordered/ranked. For example, when a course name matches a query (or a selected subject), then all the content referenced for that course is retrieved for inclusion in the list. All books or other content with titles matching the query (or the selected subject) can be retrieved for inclusion in the list.

In some cases, the relationship of search terms to meta-content, including for example in an "about" section, "summary" section, "introduction" section, "forward" section, "abstract" section and the like, may be used to determine whether a book or other content should be retrieved and ordered/ranked. In some embodiments, matches for content contained in the prefix, index, glossary, or table of contents may be excluded from the results. In some embodiments, content related to the search terms may be required to be in the content and within the index, glossary, or table of contents, which may minimize the return of results that mention a term but do not relate to the appropriate topic. In some implementations, any matching content may be returned. These content matching options may be user-selectable.

In some cases, search terms may be iteratively altered to further refine search results. For example, if a search term returns results that overwhelmingly pertain to one type or subtype of content (e.g., a search term returns twenty results from "Law" degree content and only one from "Psychology" degree content), the search terms may be altered by the educational content search and ranking engine 110 to adjust the terms to be more directed toward a different content type or subtype.

The identified educational content can be ranked by the educational content search and ranking engine 110 based on the number of times the content has been referenced. The university or other educational institution that referenced the educational content may also influence the rankings (through filtering and/or weighting the number). In some implementations, the number of references to a particular educational content item may be counted per university, per class name, and per department, for example. In some implementations, the number may also be tabulated according to class terms, for example, per year, per semester, per quarter, and per course module.

The relevant identified educational content can then be displayed at the user interface 100 in an ordered list that is ordered based on the number of times the content has been referenced. In some cases, an indication of the number of times the content has been referenced can be provided.

In one embodiment, an initial search query may not be through the UI 100 and, instead, is a result of the request from a web browser to return information from a website (providing the UI 100) at a particular uniform resource location (URL). For example, when a user enters a URL in their web browser to go to the website specifically covering the topic of psychology, the hypertext language protocol (HTTP) request for the URL can initiate a query (e.g., based on a default search query in the string or as a field of the request) by the search and ranking engine 110 and those results can be rendered in the web browser as a default result list that can be part of the UI 100 before a user enters a specific query.

Figure 3A:
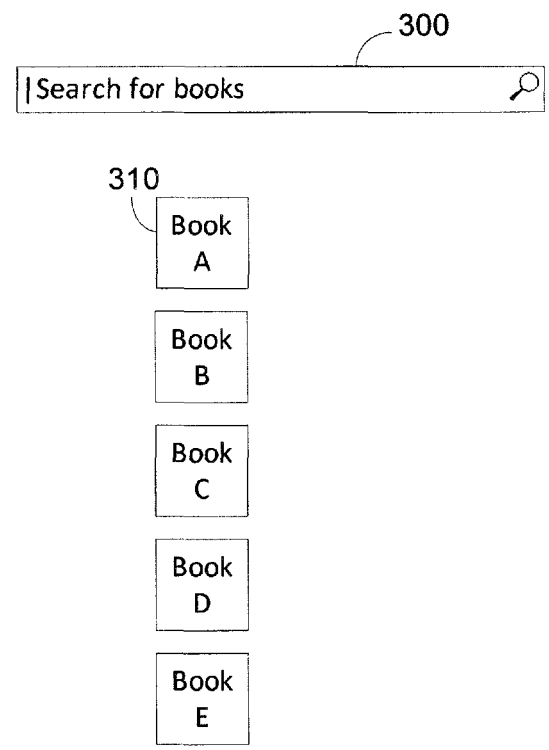
FIGS. 3A-3E illustrate example search result ordered list presentations.
Figure 3B:
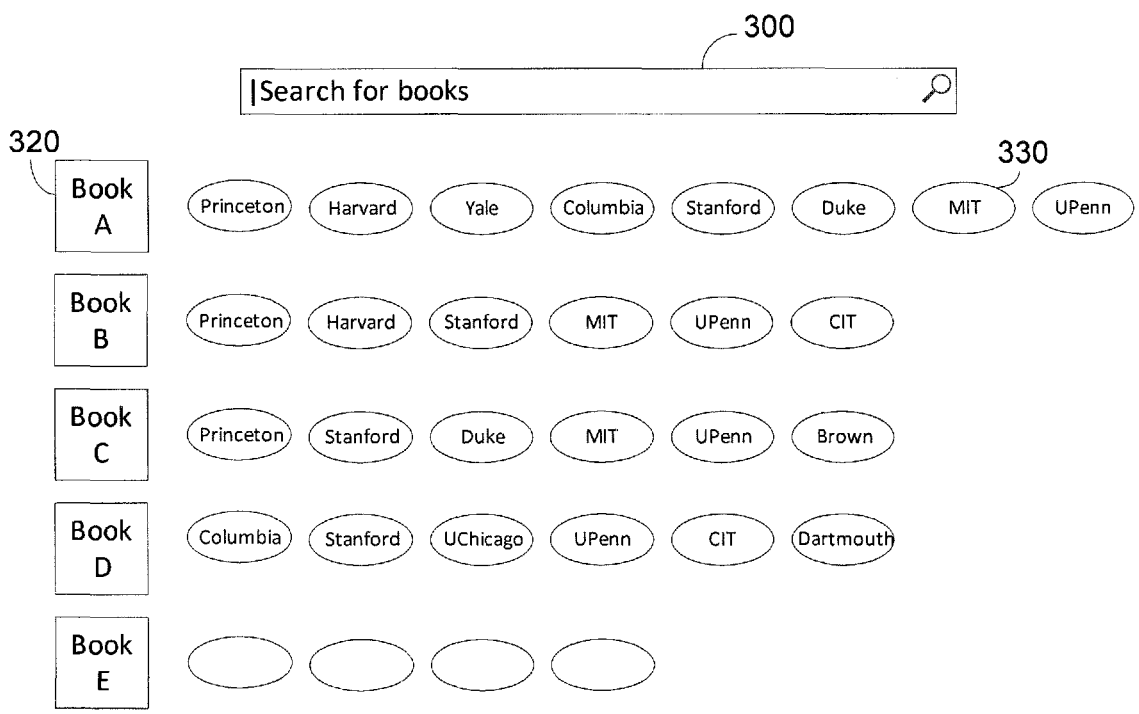

FIGS. 3A and 3B illustrate example search result ordered list presentations. Books are used as exemplary educational content in FIGS. 3A-3B, but should not be considered as limiting. In response to receiving a search query in the search input field 300 of a user interface, an ordered listing of books can be displayed. In FIG. 3A, the books 310 may be presented in a list from most referenced to least referenced. Additional filters (such as shown in FIG. 2) may be applied to further narrow the listing. Results of the search can be presented with indicators of the number of schools that referenced the book, a specific indicator (e.g., a badge or icon) for each school that references the book, the department names, each class to which the book was referenced and the corresponding school the class was in, and other information that can support the ranking of the book (e.g., provide information regarding the relevancy) and/or provide additional information that a user may use to select a text or obtain additional information.

For example, referring to FIG. 3B, the books 320 may be presented with an indicator 330 of the schools that referenced the book. In one implementation using an indicator (e.g., icon or badge) for a particular school that referenced a book, the indicator may be used only once per book even if the book is referenced by multiple courses at the school. Thus, each indicator represents that a school has referenced the book at least once. In another implementation, the indicator for a particular school that referenced a book may be used to represent each reference of the book so that multiple indicators for that particular school may be shown for the referenced book when multiple courses at that school reference the book. In another implementation, a counter may be displayed on the school indicator to indicate the number of times the book was referenced.

As mentioned above, results can be filtered. In one scenario, the results are filtered by school or a select grouping of schools. For example, the results can be filtered to show rankings based on Ivy League schools, by schools in a particular geographical region, by user-specified school or schools, by a top number of schools (as ranked by a school ranking system), or other school-related configuration.

As illustrated in FIG. 3B, each book includes an indicator of the university referencing the book. The indicators can be presented in order of the university's ranking on the U.S. News and World Report, or other university ranking system. Of course, it is contemplated that educational content from systems other than universities may be presented in addition to or in place of university-referenced content and that other schools may reference similar content as universities. Rankings for those schools and related organizations may be used in a similar manner as university rankings.

Within the results, when multiple content (e.g., books, articles, videos) in the results have a same number of sources that reference the content, the content having a same number of sources may be presented in alphabetical order. In some cases, the ranking order of tied results may be presented based on a ranking system of the schools that reference the content, such as the U.S. News and World Report. Of course, other university (and other school) ranking systems may be used. As an illustrative example, the results can be first ranked by grouping together books according to the percentage of schools that have referenced the book. Then, for ties within the same ranked books, the books that have a book title that matches key word(s) of the search may be presented first or the books that have the most class name matches to the key word(s) of the search may be presented first.

"Most class name matches" may be determined multiple ways. For example, every school with at least one class name match could count once and only once; then a ranking can be made between the schools to generate a school's class ranking within a named class ranking. As another example, across the board class name matches can be counted for the book as looked at across all schools referencing it. As yet another example, duplicate class names within a school would only count once. Of course, other tie breakers may be used.

Further ties may be broken by the average U.S. News and World Report rankings of the schools referencing the book, and ties still there may be broken by the highest ranked individual school of the tied books, and ties still there can be broken by the ABC order of the book titles.

Other non-limiting examples of tie-breaking methods include incorporating user reviews or ratings of content (where content have a 5 out of 5 star rating would be listed before content having a 4 out of 5 star rating).

In some scenarios, when multiple books have a same number of sources referencing the book, then these books can be ranked according to title first (e.g., percentage of key word(s) found in the title), and then by text within each book (the percentage of key word(s) or the number of times a term or topic is found within the textbook or within pages of the textbook that have been referenced). Books may also be ranked based on class/course name. For example, a school may have different courses that reference a same book. The search results can return books that are referenced to class names that are associated with the keywords of the search. If ten books are referenced by 5 schools each, these ten books can be ranked in alphabetical order of book title. In some cases, the books can be ranked by a combination of most relevant book titles and most relevant course titles (to the keyword(s) of the search), book title only, or course title only.

In addition, one or more tie-breaking methods may be applied to the listings of the results where a first tie breaking method does not break all the ties. As a non-limiting illustrative example, for ties within the same ranked books, the books that have a book title that matches key word(s) of the search may be presented first. Then, for the books that are tied for a same position, the books that have the most class name matches to the key word(s) of the search may be presented first. The books that have the most associated class name matches to the key word(s) may determine the next ordering both within the matched book title group and outside of the matched book titles group. Ties within these groups may next be broken by averaging the U.S. News and World Report rankings of the schools that referenced the books; higher averages can be listed before those with lower averages. For remaining ties, the highest ranked school that referenced the books can be used to order the books. Then, if there still remains a tie, the ABC order of book title may be used.

However, indicators may show other ranking criteria for educational content. For example, professor name, class name, major, minor, degree, and department indicators may be shown in some cases, depending on the criteria for ranking. In some cases, more than one type of indicator may be shown, and the indicators may be grouped by type. Groups of badges may include, for example, groups for the schools, professors, and classes using the content.

Figure 3C:
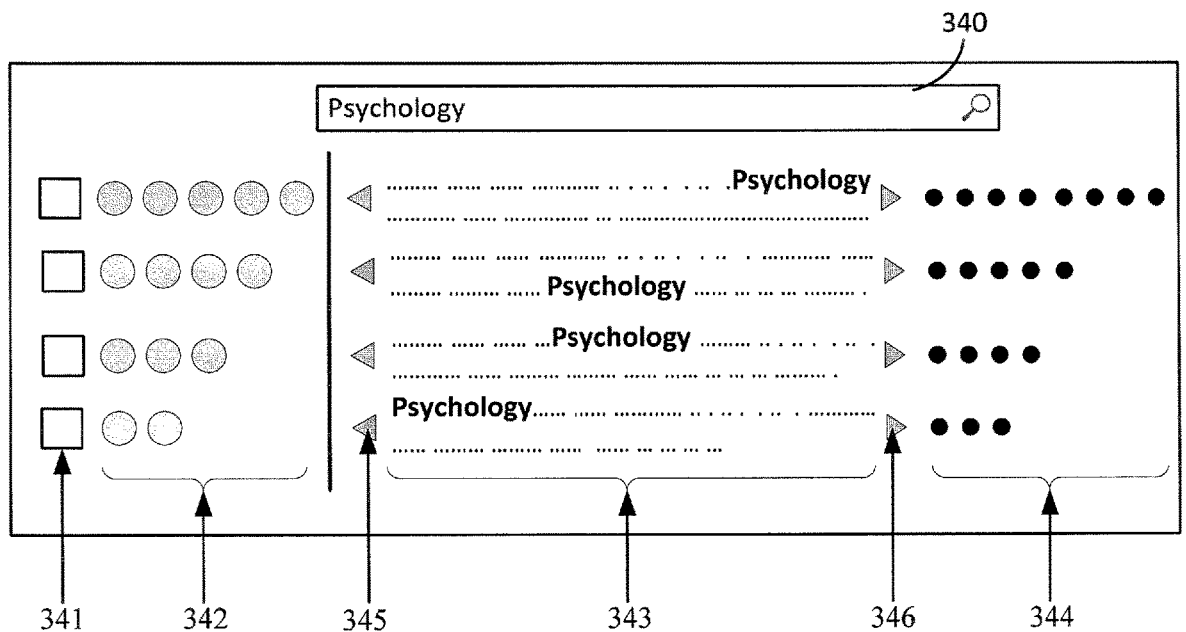

FIG. 3C shows an example ordered search result list presentation that may be used in some implementations. An interface is shown in FIG. 3C that contains both ranking information and the ability to navigate the textual content. The results for an example search of content related to "psychology" 340 are shown. A line in the result list shows a particular piece of educational content, such as a book or article. An area for depicting a visual icon of the content 341 may be available, as are ranking indicators 342. Reflecting the fact that ranking indicators 342 may be of multiple types and groupings, as discussed, the ranking indicators 342 are shown here without specific content, unlike as in FIG. 3B.

Textual content 343 may also be navigated within the search result presentation. One or more page locations, depicted by locator icons 344, may be shown. In the figure, locator icons 344 show pages in the educational content having the search term "psychology." Selecting a locator icon may navigate the textual content 343 interface to the location in the content having the search term. Here, the textual content 343 interface shows "psychology" and a number of words in the text around the term. Navigation arrows (345, 346) may be available to move forward and backward within the text.

Figure 3D:
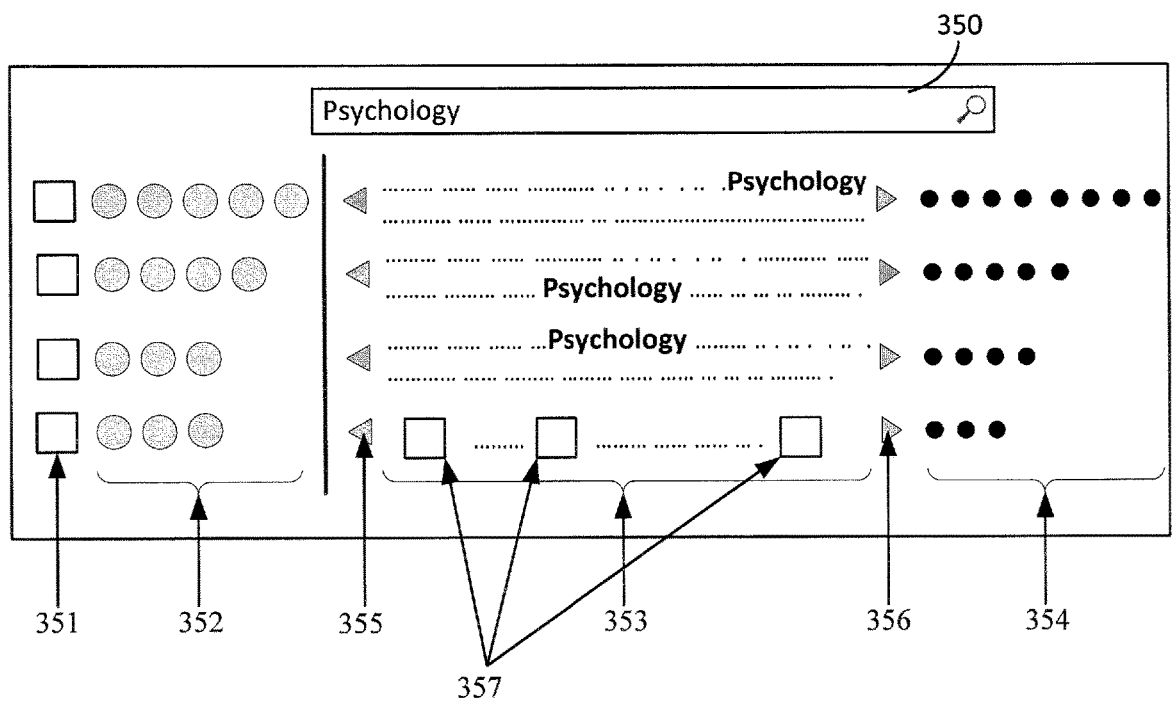

FIG. 3D shows a variation on the interface of FIG. 3C, where textual content is replaced by audio or audiovisual content. In FIG. 3D, one of the returned educational content results is a video. Familiar elements such as an icon 351, indicator badges 352, content review area 353, locator icons 354, and backward and forward arrows (355, 356) are shown, as in FIG. 3C. However, in the video content review area 353 for the video content, video clip segments are depicted using clip segment indicators 357. The clip segment indicators 357 may enable easier navigation to review the assigned time segments for a video type of educational content. As the interface in FIG. 3D shows, it is possible to navigate mixed content types in an example interface having these characteristics.

In some situations, it may be desirable for a user interacting with the user interface 100 to select individual items of content from a listing of search results so that several content options may be narrowed, compared, or searched further. The additional selections of content may form a user-created list of results that may then be searched and/or ranked further. For example, if a search of "psychology" returns a listing of content from several classes that include "psychology" in the title, only some of the content may be relevant to the user if the user only wants basic psychology content. The user may select the content that seems to fit his or her desired content. In some embodiments, the user's selection of content may form the basis for a user-defined result list that displays ranking information with respect to only the user's selected content. Some embodiments may enable additional searches by the user with respect to only the selected content. Some embodiments may allow the user to execute a function to find additional content using the selected content as a model for the search and ranking engine.

Figure 3E:
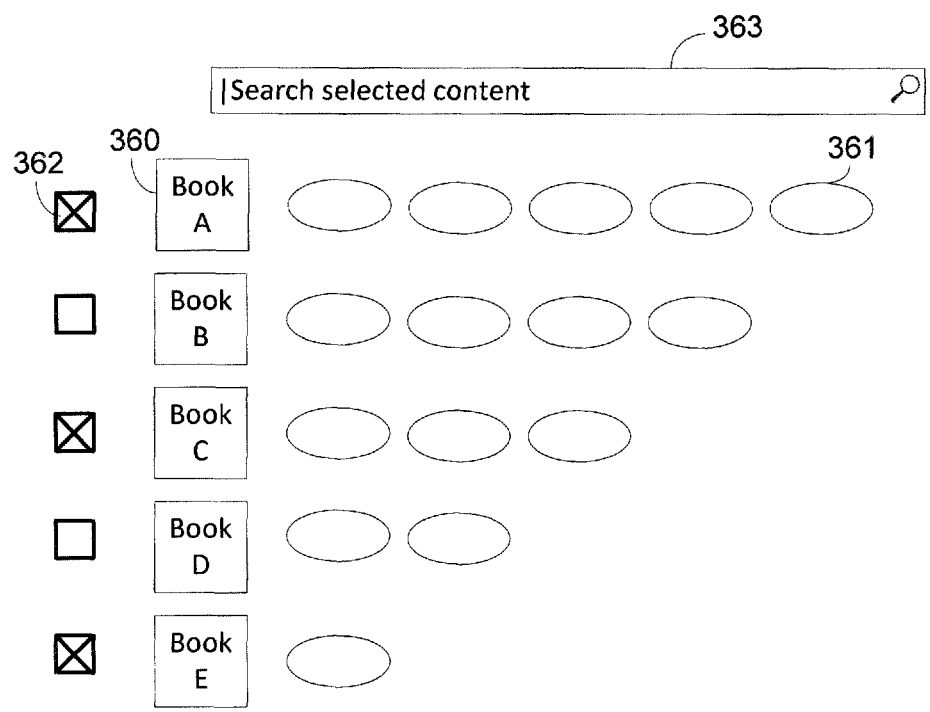

FIG. 3E shows an example of an embodiment that allows further selection of search results. In FIG. 3E, educational content 360, which may in some embodiments include ranking indicators 361, may be individually selected from the search results using additional interface elements. Checkboxes 362 are shown as examples of interface elements that may allow selection, but various kinds of interface elements may be used, as practitioners will appreciate. Selection of the results by the user may allow the user to create a secondary list that may then be ranked against one another using the described techniques. Additional interface options, such as a search box 363, may also be available to run searches against only the selected content items.

Figure 4:
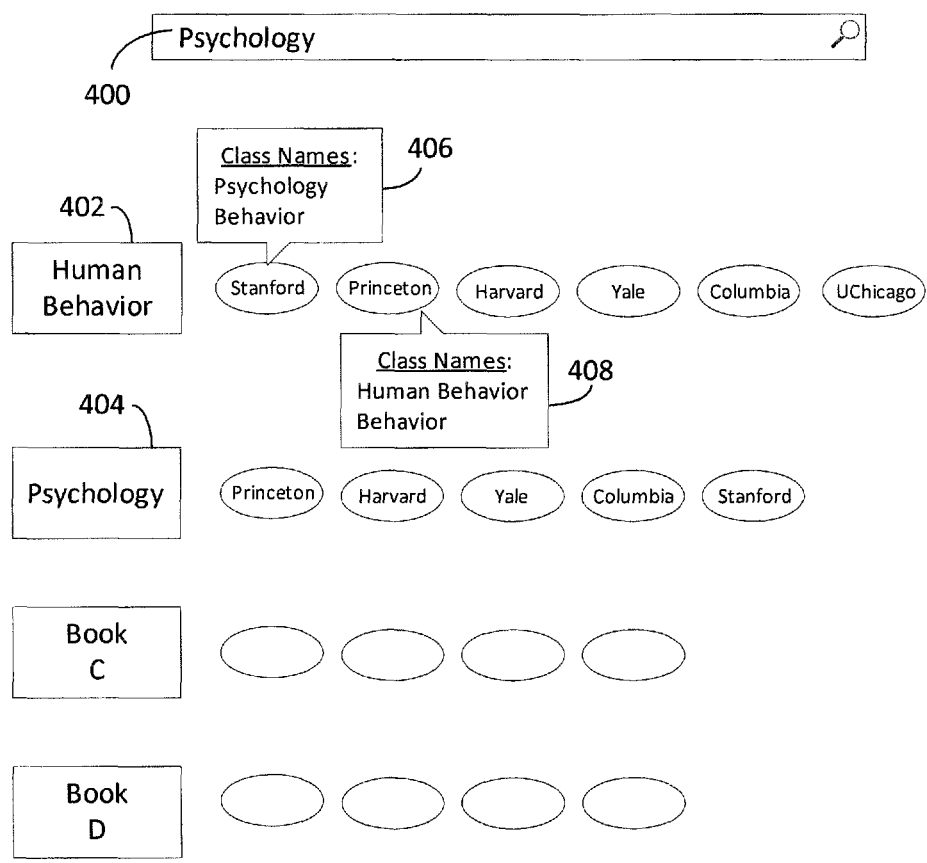
FIG. 4 illustrates an example search result.

FIG. 4 illustrates an example search result for a search of "psychology." For example, a user may enter "psychology" as the search query. The system then searches the database (or other structure such as a table) for books associated with "psychology." From the books associated with psychology, the most referenced books associated with a set of sources, for example 50 schools, can be presented in order from highest number of references to lowest number of references. The results can include a book titled "Human Behavior" 402 and a book titled "Psychology" 404. In the illustrated example, school indicators are included to show the universities that assign or recommend the book. For the book "Human Behavior," Stanford, Princeton, Harvard, Yale, Columbia, and the University of Chicago have all referenced the book.

In this FIG. 4 example, class titles are searched first, and then book titles. Other implementations may take a different order. The book "Human Behavior" is identified (along with other content) from a search of class titles with the term "psychology" because Stanford includes a class name of "Psychology" 406. Indicator popups (406, 408) may show additional information about the selection criteria for an indicator ranking, for example, by showing the class names for which the educational content was chosen. In the figure, for example, the indicator for Stanford is shown before the indicator for Princeton even though Princeton ranks higher on the U.S. News and World Report ranking because one of Stanford's class names matches the search term, whereas Princeton's class names 408 for classes that reference the text book "Human Behavior" do not include the word "psychology."

Other information may be displayed in indicator popups 406 and 408. For example, indicator popups 406 and 408 may show professor names, professor rating metrics or scores, class names, educational source names, department information, major information, degree information, minor information, page citation counts, or other information that may be used to understand the basis for ranking indicators. The content in indicator popups 406 and 408 will, of course, vary by the nature and type of indicator used shown in the results presentation.

Figure 5:
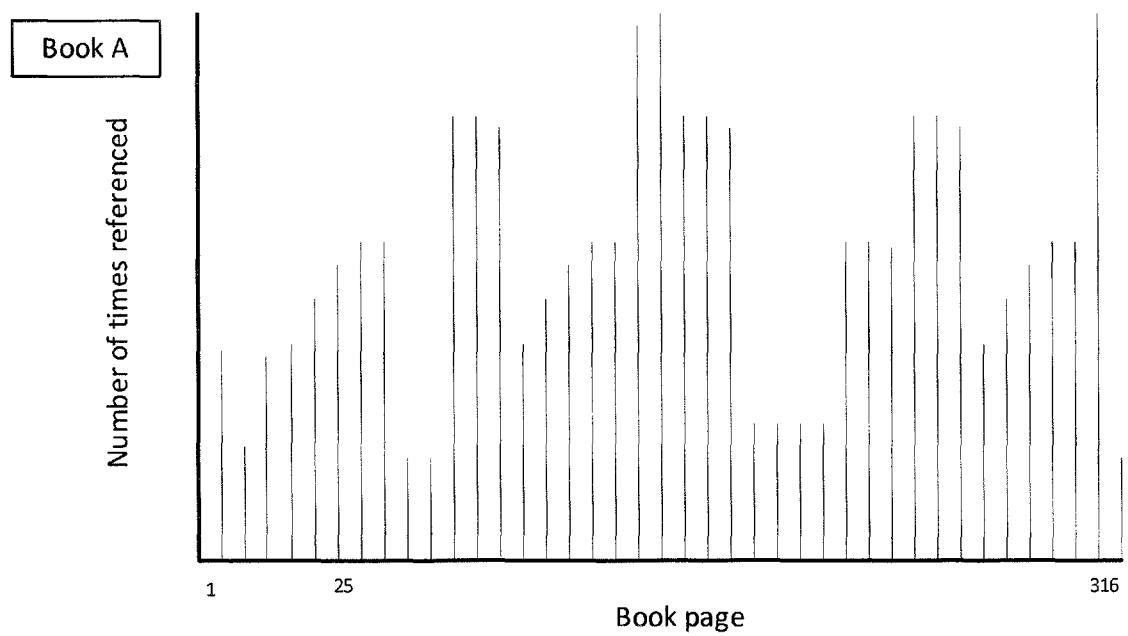
FIG. 5 illustrates an example user interface including a page graph.

FIG. 5 illustrates an example user interface including a page graph. In some implementations, additional information about referenced sections/chapters/pages of the text can be presented. FIG. 5 shows one manner of presenting information about the referenced pages, where a plot illustrates the number of times a page is referenced as part of the reading for a class (and across all classes or selected classes referencing the book). In some implementations, an independent page number on the graph can only go up/increase in relevancy in regard to being referenced, once per school, so as to make identical page references from a single school only count once while allowing different page references from classes within the same school to count. Then, when a separate school also references the page that has already been increased on the graph, the graph increases in relation to that page number of the book. In another implementation, the graphed page number(s) go up every time a non-identical class name within an independent school references the page(s). Different schools with a same named class are each counted, which allows for identical class names from separate schools to increase the page count on the graph.

In some implementations, a page graph may depict timing ranges in a video, audio, or other recording. The graph could show minutes or seconds rather than pages, if minutes are relevant to the content type. For example, if a class is assigned to watch a particular range of minutes in a particular video, the ranking would be increased for each class referencing the minute range. The count might be visually depicted using a graph similar to the page graph, but showing minutes or seconds instead of page numbers.

In some implementations, a page graph like the example shown in FIG. 5 may be presented in conjunction with other user interface elements so that page graph information may be compared between educational content. For example, a page graph may be displayed as an interface element of FIG. 3C for each returned educational content.

Figure 6:
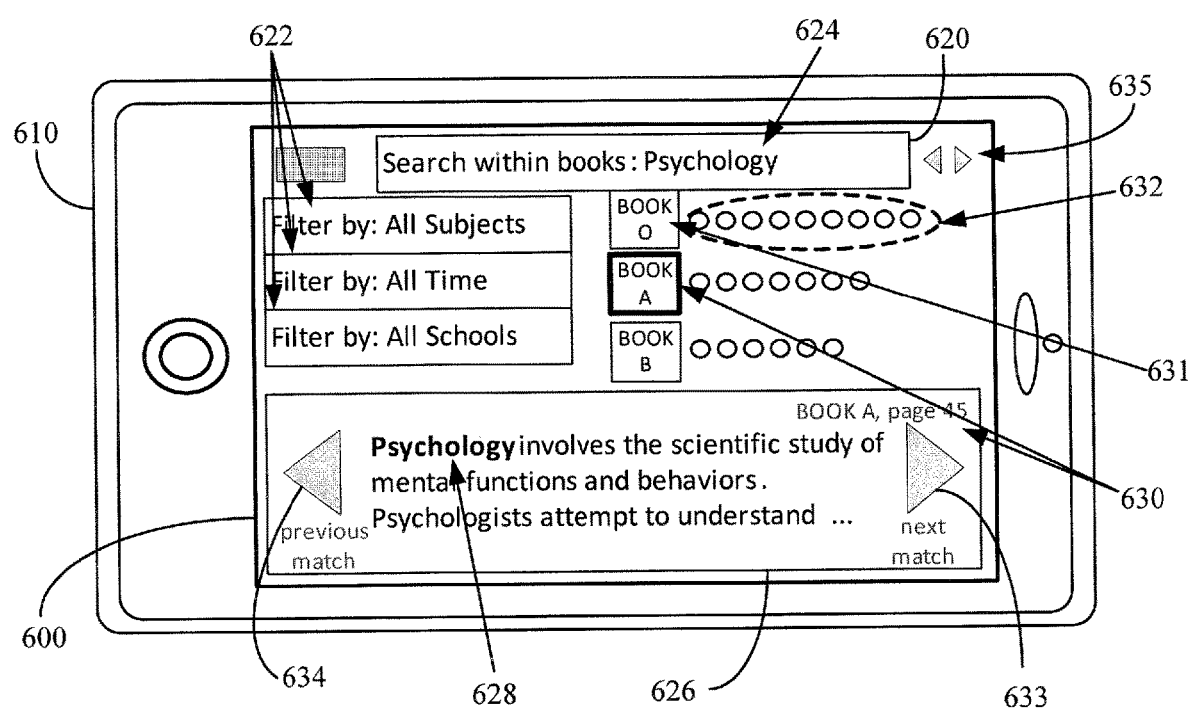
FIG. 6 illustrates an implementation of a user interface for small form factor devices.

FIG. 6 illustrates an implementation of a user interface for small form factor devices. Referring to FIG. 6, a user interface (UI) 600 for the educational search and ranking engine is shown that is suitable for a touch screen device 610, such as a smart phone. The UI 600 may include a search bar 620 and optional filters 622. Although three filters 622 are shown, these filters are presented for illustration and are not meant to be limiting in types (what is being filtered) or in number of available filters. In the example shown in FIG. 6, a query to search within books for "Psychology" 624 has been entered into the search bar 620. This screen may be in a state after a search for matching word(s) within a book has been conducted. A previous screen may be a home page that includes an ordered ranked list of all available content or a subject-specific (e.g., the subject of "Psychology") screen with a listing of content related to that subject. Of course, the page shown in the figure may be the originating screen.

In some cases, when searching within books, the UI 600 can include a preview 626 of the book(s) providing relevant text. For example, the matching term "Psychology" 628 from Book A (630) may be indicated along with a portion of the text around the matching term to provide context before a user selects to view the book 630, access more information about the book, or view another section either within Book A 630 or another book containing a matching term. In the example shown, a listing of books is also shown on the same screen as the preview 626. Here, three books, ranked according to any of the techniques described herein, are shown. Book O 631 has the most references (indicated by icons 632 representing the schools referencing the content), followed by Book A 630. After the user conducts a within-the-book search, the within content word match(es) with the highest ranking may be shown. The user may navigate through the content by selecting a next match 633 or previous match 634 for the preview 626 and/or by selecting a book from the ranked listing of books (either directly by selecting on the book icon or by indicating a next or previous (635) book.

In FIG. 6, and in all content embodiments or within content preview embodiments and the like, there can be arrows that traverse to next or previous page, arrows for traversing to next or previous ranked page, and arrows for traversing by matches of the content based on page rank of matches (in some embodiments, navigation may start at the top of a page when there are multiple matches on same page or preview) and arrows for traversing by matches of the content front to back. In some embodiments, arrows may not be required and changing preview may be navigable like pages in a book, or traversed by rank of pages regardless of if there is a match or not. Some implementations could have arrows that allow for next or previous page or traverse pages based on rank of page regardless of if there is a match on the page, or implementations wherein both can have arrows for both methods of traversing represented simultaneously.

The systems described herein may be carried out in a manner that facilitates free (from a user perspective) consumption of the educational content. In some implementations, a search within text of a book or other educational content can be provided for free to users by paying the content provider(s) (e.g., the copyright owner or publisher) a percentage of the ad revenue that is derived from advertisements shown when a user "opens" the book via the search within a book. The position/ranking of the book or other content on the list may also affect the payment. In addition, the type of content (e.g., video, book, article) may affect cost. Other considerations that can affect cost include the popularity of a piece of content, whether a specific piece of content is selected by an advertiser or a grouping of content is selected, and length of advertisement.

A user may be able to traverse text through a command indicating a request to view a next relevant location, for example by clicking on a button (e.g., via touch or mouse) or by voicing a command that brings the user to a next or previous place in the book that matches the search or to the next or previous most referenced book that has the text match within the text of the book, which will enable the user to search within the text of all books for free. The user can be presented with only the page on which the text matches as well as the page before and after the matching page. In another case, the user may access the text of a book for a period of time, for example 30 minutes, before the user is presented with another ad. Another advertisement may be shown at each 30 minute interval. The cycle may begin again for each book (or other content) that the user views. Alternatively, the advertisement interval may be per user time, resulting in the user being able to view any content and receiving an ad every 30 minutes regardless of the particular piece of content that the user is viewing. Time spent viewing a particular piece of content can still be tracked to facilitate the determination of the amount being paid to a content provider for access to the content.

In another case, the user may access the text of a book until a specified number of pages have been viewed. Then, the user would be presented with another advertisement if they want to keep reading within the text, and the cycle may be repeated. When a user "opens" another book, a new ad can be run, allowing the user to view a specified number of pages before another advertisement is shown. Alternatively, a user may be given a set number of pages that they may access after viewing an advertisement so that they may view any number of books (or other content) until the set number of pages (regardless of being different books or content) have been viewed. Pages viewed at a particular piece of content can still be tracked to facilitate the determination of the amount being paid to the content provider for access to the content.

Advertisements may be of different lengths and types. In some cases, the first advertisement to which a user is exposed may be shorter than subsequent advertisements. In some cases, the length of time for an advertisement may be based on the content. Of course, other factors may contribute to the length of time for the advertisements.

In one scenario, auctions may be held periodically for advertisers to place their bids to have video or other ads shown for all content or specific content. Advertisers may place bids for a specific one or more pieces of content, a presented grouping of content, or all available content. The bids may involve placing money in escrow; otherwise payment may be made upon winning the bid. The advertising bids for the content are for enabling advertisements associated with the content for a specified period of time or a specified number of views or plays. After the time that all the bids are due from the advertisers, the winning bid for each piece of content goes to the highest dollar amount bidder and the highest bidders will then be able to show their ad during the specified period of time (or for the specified number of views or plays).

In some cases, there could be a situation where there is a tie in an amount placed as a bid for a particular piece of content. This scenario may occur where bids are submitted blind (e.g., there is no knowledge of other bids) or where bid amounts are not updated as fast as they are submitted. An additional period of time may be provided for those advertisers to bid until a highest bidder is achieved (or the additional time period ends). It is also contemplated that a winning bid could be selected in some other manner that may not be based on the bid being the highest.

In some implementations, an advertiser may select when (e.g., time of day, day of week, after/before a particular location in content), how (e.g., type of advertisement—video, still image, interactive advertisement; how often), and who (e.g., type and/or location of user based on a log-in information of the user or based on internet protocol (IP) address of user) receives the advertisement.

In some implementations, a user may be logged-in while accessing the system and searching and/or reading educational content. In some implementations, cookies may be stored at the user's device so that when the user returns to the website providing the user interface to the educational search and ranking engine, the system can recognize that the user has been on the site before and may even recognize that the user has "opened" some content. A history log or other record may be maintained so that the user can see what content has been reviewed and may more easily return to already viewed content. In some cases, the farthest location and/or bookmarks may be stored for the user so the user may return to a location within content.

Medical Content

People sometimes turn to the Internet to find out more about the options for treating their medical condition or symptoms. Searching for medical content and information over the Internet can be difficult because it is not easy to determine whether a medical device, drug, therapy, or treatment is most appropriate for a given set of medical problems or symptoms. Although there are a number of websites that purport to provide medical information, a search of this content is generally conducted directly using key terms input to a search bar.

Unfortunately, it is not always possible to determine which of a number of results would be the most likely one to be helpful in ameliorating a given medical problem. Sometimes results are ranked according to relevancy, but the relevancy ranking may only be a function of a number of times a term is found in the text of an article about a medical problem. In some cases, there may be reviews of the medical content which can help inform the decision. However, the trustworthiness of the suggestion or review may be difficult to determine.

In embodiments describing or pertinent to medical content, systems and techniques for facilitating medical content search and results are described. The medical content can be presented in a manner that indicates trustworthiness or relevancy based on the frequency of reference (e.g., purchase, use, prescription, or recommendation) by a healthcare provider. By providing searchers of medical content with information indicating the number of actual uses of, for example, a medical device, pharmaceutical, or therapy, the searcher may better evaluate the usefulness of the search results.

The medical content being referenced can include, for example, medical devices, medical products, pharmaceuticals, medical procedures, medical therapies, and medical treatments. The various kinds and categories of medical content may be known herein as "content types." Individual instances of medical content—e.g., a particular product like a pacemaker—may be sometimes known as an "item of medical content."

The healthcare provider referencing the medical content can include, for example, a hospital or other medical facility, doctor or other healthcare professional, and a pharmacy. A medical facility can include, for example, a hospital, clinic, outpatient surgical center, practitioner's office, urgent care facility, medical school, medical institution, mobile care center, physical therapy center, laboratory, diagnostic center, medical research center, gymnasium, and animal hospital. A healthcare professional may be, for example, a medical doctor, surgeon, specialist, nurse, nurse-practitioner, physician assistant, dentist, psychologist, psychiatrist, physical therapist, rehabilitation therapist, certified trainer, optometrist, osteopath, chiropractor, and veterinarian. The various kinds and categories of healthcare providers may be known herein as "provider types" or "healthcare provider types."

A healthcare provider may reference medical content in several ways, some non-limiting examples of which are described below. For example, a healthcare provider may purchase a medical device or medical equipment for use in a medical facility or medical procedure. A healthcare provider (such as a doctor) may use a medical therapy, medical device, medical procedure, or medical treatment on a patient or in a medical facility. A healthcare provider may prescribe a drug or non-drug therapy to a patient to ameliorate an ailment. A healthcare provider may even recommend a lifestyle change or other course of action, such as that the patient intake less salt, to assist in treating a symptom or disease.

An instance of "referencing" (e.g., purchasing, using, prescribing, and recommending) a medical content may be counted such that ranking of the references associated with a disease, symptom, or side effect are possible. A brief example may be illustrative: A patient searches for the ailment "hypertension" using the described systems and techniques. The search may return ordered medical content results showing that, for example, 99 healthcare providers recommend reducing salt intake, 95 recommend stopping smoking, 91 recommend more exercise, and 48 prescribe the hypertension-reducing drug X and 28 recommend the hypertension-reducing drug Y. Presenting results in this manner may assist the patient in evaluating therapeutic options by referencing the actual behavior of healthcare providers. "Using" may include "wearing," as when a healthcare professional wears a particular brand of gloves or other personal protective gear; using may also include conducting, administering, or employing in some way; for example, a hospital might use a particular kind of anti-microbial mousepad for its computing systems, or particular software for handling patient intake data.

The manner that a medical content is referenced (sometimes known herein as a "reference type") may in some implementations affect how the medical content is ranked and/or counted. For example, certain medical products, procedures, treatments, therapies, or drugs may be indicated as "prescribed," whereas others may be suggested as "recommended." Some products may be medical supplies or techniques purchased or used by a facility. In some implementations, all or a subset of referenced medical content are included as part of the results. In some implementations, only the prescribed content are included as part of the results. In other implementations, only the recommended content are included as part of the results. In some implementations, the manner in which the medical content is referenced is indicated as metadata associated with the particular content.

In some cases, a weight may be assigned to the medical content (for the rankings) based on the manner in which the content is referenced. In some cases, no distinction based on the manner in which the content is referenced is made in the rankings. In other cases, "prescribed" may be weighted over "recommended" content, for example. In yet other cases, a distinction may be provided between "prescribed," "recommended," "purchased," and "used" medical content through use of an indicator in the search results. Accordingly, it should be understood that the content ranking may be based on the manner in which content is referenced by a healthcare provider; and when reference is made to "referenced" medical content any combination of medical content used, purchased, prescribed, recommended, or otherwise utilized for a disease or symptom may be included in all permutations.

In some implementations, only "prescribed" content is presented for a user. In some implementations only "recommended" content is presented for a user. In some cases, only "purchased," or only "used" content may be presented for a user. In some implementations, any combination of purchased, used, prescribed, or recommended content may be presented for a user. In some implementations where medical content having multiple types of reference are presented to the user, the system may be agnostic about how the content is referenced and may present results as if there is no difference between the types of reference. In some implementations where more than one type of referenced content is presented to the user, the manner in which the content is referenced might not affect how the content is ranked, but can be indicated to the user so that the user knows whether the content was purchased, used, prescribed, or recommended by a healthcare provider. One way of indicating the manner in which the content was referenced is to include a particular icon, popup, or other indication in association with an indicator of the healthcare provider (or other level of granularity relevant to the healthcare provider) that referenced the content.

In some implementations where content having multiple reference types are presented to the user, the manner in which the content is referenced can affect the rankings. For example, each "prescribed" reference to a piece of content may be weighted differently than each "recommended" reference to that piece of content. As another example, the number of prescribed references to an item of medical content may be used as a tie-breaker when two pieces of content have a same number of total references, but differing numbers of prescribed references (e.g., both pieces of content have 10 references, but one was referenced as prescribed 7 times and the other was indicated as prescribed only 6 times—the remaining references being recommendations). Modifying rankings through weighting or tiebreaking in accordance with prescribed and recommended reference types of course extends to other reference types (e.g., purchased and used).

In some implementations, the type of medical content may affect the rankings through weighting. For example, when multiple types of medical content are presented to the user (e.g., mixed results of drugs, medical devices, procedures, and therapies), one or more types of medical content may be weighted differently than other types. For example, a medical device may be weighted higher than a drug therapy.

The information about medical content referenced by a healthcare provider may be gathered from a variety of medical content referencing data sources. Sources of referencing data may be a medical facility or healthcare provider information system, such as a system used to chart patients, patient outcomes, or healthcare professionals' activities. Medical insurance databases may also be sources of referencing data. Medical device or pharmaceutical sales and inventory databases may also be sources of referencing data for medical content. Government databases, such as may be provided by the Centers for Disease Control, may be sources. Research databases containing demographic or epidemiological information may be sources, as well as databases containing genetic results such as associations between genomes and disease prevalence. Consumer data provided by data brokers from ad tracking or other data mining activity may also be sources. In some cases, information about individual patients may be masked or anonymized to ensure patient privacy and compliance with medical privacy statutes. The medical content referencing data sources described above are illustrative only and should not be considered as limiting of the types and varieties of information systems that may be a source of medical content referencing data by healthcare providers.

Figure 7:
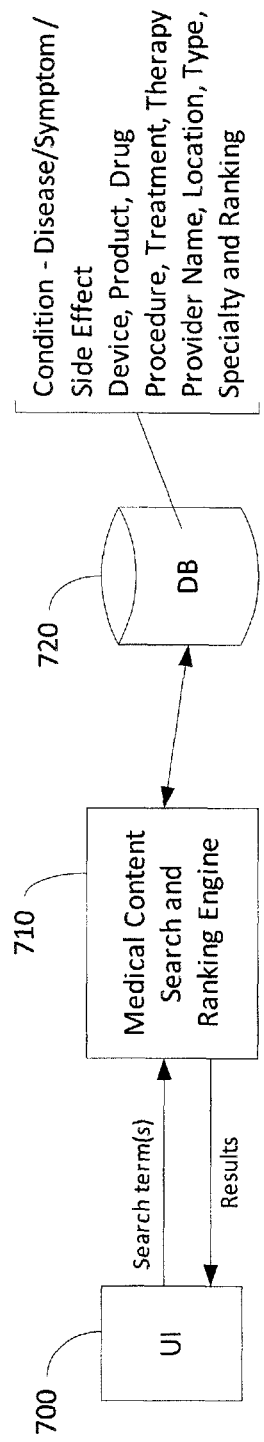
FIG. 7 illustrates an operating environment in which certain embodiments may be implemented.

FIG. 7 illustrates an operating environment in which some embodiments may be implemented. Referring to FIG. 7, a user may conduct a search of medical content through a user interface (UI) 700. The search can be conducted on diseases, conditions, symptoms, side effects, medical therapies, medical devices, medical products, pharmaceuticals, drugs, properties of drugs and pharmaceuticals, medical procedures, medical treatments, or a combination of one or more of these categories. The areas for the search may be specified by the medical content search and ranking engine 710 (e.g., via a drop-down menu) or may include free-form input provided by the user via the UI 700 (e.g., via a search bar).

Figure 8:
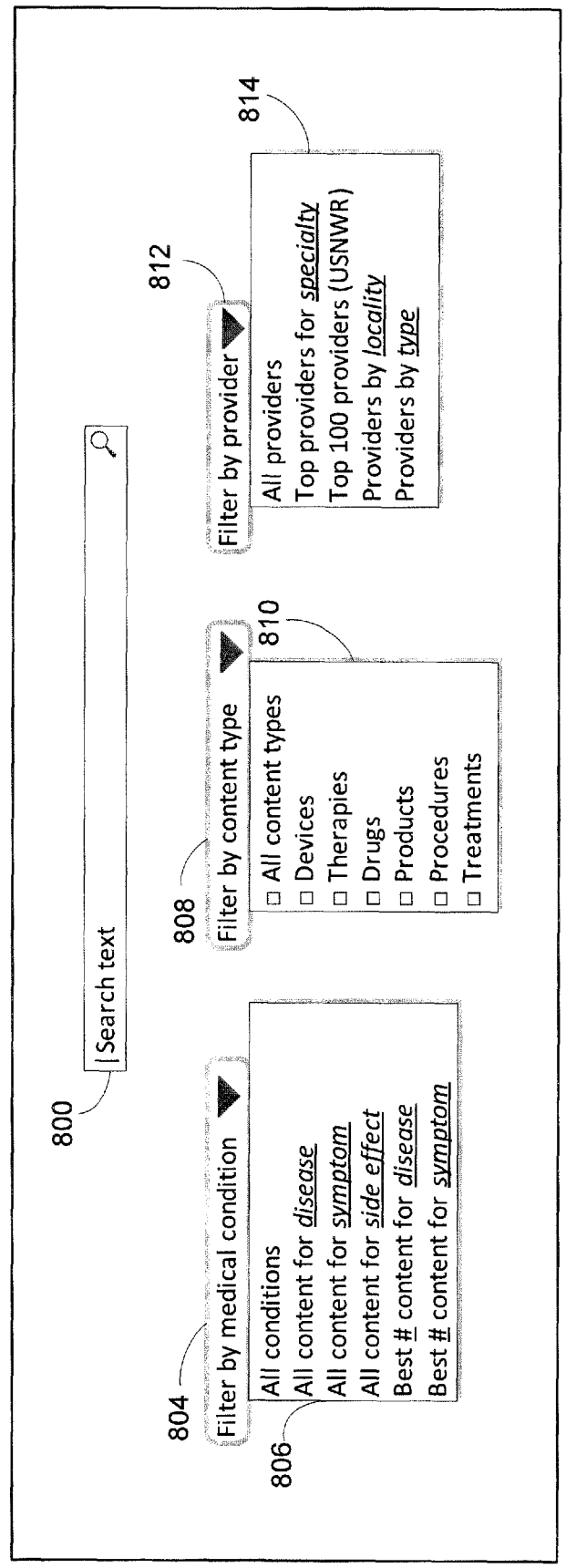
FIG. 8 illustrates an example user interface of a search page for medical content.

The user interface may include features as illustrated in FIG. 8. As shown in FIG. 8, an input field 800 can be provided for receiving a search query for medical content. As noted, the input field 800 may allow searching of a wide variety of medical content, as well as searching medical content by diseases, conditions, symptoms, or side effects to which medical content may be associated.

In some implementations, users do not need to do a search to access the content as the content may be listed in a default or otherwise optimized manner before a specific search is entered by the user. In some implementations, an ordered listing of content can be presented on a landing page (e.g., "home page") of a medical content listing website rendered in a user's browser application (and providing a user interface to the medical content search and ranking engine). The default ordered listing may be, for example, of content for the top diseases, conditions, or side effects ordered by the frequency or incidence of the disease, condition, or side effect within a given population (as known from the database or other structured data stored on a resource for the medical content search and ranking engine). A default ordered listing may also be, for example, the top prescribed, recommended, purchased, or used medical content for a given population. In some cases, demographic characteristics of the user may be used to determine the relevant population.

In some implementations, user-adjustable filters may be used to narrow, refine, or reorder the results before a search is conducted or after the search is conducted.

A "filter by medical condition" 804 can provide filtering options 806 such as, but not limited to, enabling a search of content for all conditions, all content for a specified disease, all content for a specified symptom, all content for a specified side effect, a designated number of highest ranked content for a specified disease (e.g., "top 10 content for hypertension"), and a designated number of highest ranked content for a specified symptom (e.g., "top 25 content for headache") as some examples. In some cases, the disease, symptom, or side effect being filtered may be indicated by the text in the search text input field 800.

A "filter by content type" 808 can provide filtering options 810 such as—but not limited to—enabling a search of all content types, or a search of one or more individually selected content types, for example medical devices, therapies, drugs, products, procedures, and treatments. Sub-types are also possible, including, but not limited to, controlled substances, over-the-counter products, herbal substances, in-patient procedures, and out-patient procedures. In some embodiments, sub-types may include sub-components or properties of content types. For instance, pharmaceuticals may be filtered by such further sub-components as "active ingredient" so that, for example, particular classes of chemical the user is allergic to may be excluded. In another instance, if medical cannabis is returned as a result after a search for "epilepsy," additional filtering options may filter the cannabis types by properties such as type of administration or formulation (e.g., dried leaf/flower, oil, pill form, chewable, extract, concentrate), botanical categorization (e.g., leaf), strength (perhaps because a milder cannabis may be needed for a child with epilepsy). Other sub-type filters may be envisioned depending on content type.

A "filter by provider" 812 can provide filtering options 814 such as, but not limited to, enabling a search of all providers (e.g., medical facilities and healthcare professionals), for top providers in a designated specialty (e.g., "top cancer hospitals" or "top oncologists"), for the top 100 (or other "top" number) providers according to a designated ranking service (e.g., "top 100 providers from the U.S. News and World Report (USNWR) rankings"), for providers by designated locality (e.g., "providers in Florida"), and for providers by a designated type (e.g., "outpatient orthopedic surgical centers") as some examples. In some cases, filtering can be according to insurance policies.

Other filter types (not shown in FIG. 8) are also possible, enabling further filtering of some results. In some embodiments, available filter options may be determined or dynamically redefined by prior filter selections, as for example when selection of a "symptom" filter surfaces an additional filter based on different symptom names or categories. In some cases, a filter selection may initiate the display of an additional interface or interface element. For example, a "product" content type may initiate the display of an interface for navigating product subcategories, such as "pacemakers," "stents," or "artificial valves."

Of course, other designations may be provided and even natural language queries may be used in certain implementations. The described search and ranking engine may be accessible via a personal assistant such as Siri® available from Apple Inc., Google Now™, or Cortana® available from Microsoft Corp. Queries may be input through voice commands or by touch or text or other input. The manner of applying the filter(s) may be any suitable tool bar, input field, or menu for providing the information.

Returning to FIG. 7, search terms entered via the user interface 700 are used by a medical content search and ranking engine 710 to search a database (DB) 720. The database 720 can include structured information regarding medical content. A wide variety of medical content information may be stored, some of which may support the use of filtering categories described above. The database can be generated, for example, based on data provided by healthcare providers, insurance companies, consumer data companies, medical device manufacturers, medical product suppliers, pharmacies, and medical researchers.

The medical content search and ranking engine 710 can use the search terms provided via the user interface 710 to identify relevant medical content from the database 720. The identified medical content can be ranked by the medical content search and ranking engine 710 based on the number of times the content has been referenced.

Characteristics of the healthcare provider that referenced the medical content may also influence the rankings (through filtering and/or weighting the number). In some implementations, the number of references to a particular medical content item may be counted per provider, or may be subdivided by medical facility and healthcare professional.

The relevant identified medical content can then be displayed at the user interface 700 in an ordered list that is ordered based on the number of times the content has been referenced. In some cases, an indication of the number of times the content has been referenced can be provided. In some cases the indication of the number of times the content has been referenced may be tabulated per healthcare provider. The listing within the UI 700 can show trending, such as new surgical techniques or medications. Recent trends can affect the weighting—for example, bypass surgeries may have dominated 20 years ago, but angioplasty and stent implants are the dominant trend today. The relevant identified medical content can also reflect recent FDA approvals.

In one embodiment, an initial search query may not be through the UI 700 and, instead, is a result of the request from a web browser to return information from a website (providing the UI 700) at a particular uniform resource location (URL). For example, when a user enters a URL in their web browser to go to the website specifically covering a designated disease (e.g., "lupus"), the hypertext language protocol (HTTP) request for the URL can initiate a query (e.g., based on a default search query in the string or as a field of the request) by the search and ranking engine 710 and those results can be rendered in the web browser as a default result list that can be part of the UI 700 before a user enters a specific query.

In one embodiment, an initial search query may not be through a UI 700 and, instead, is the result of a request from a mobile device application connected through a mobile device to a biometric sensor. For example, a user may be wearing one or more biometric sensors to detect, e.g., pulse, blood oxygen, airflow, body temperature, galvanic skin response, patient position, or heart rhythms. The biometric sensors may be connected to a mobile device running an application that may send queries to the medical content search and ranking engine 710 (for example, via HTTP, as noted above). Search results of medical content may be presented to the user via UI 700 when an out-of-boundary biometric condition is detected by the application via the biometric sensors. As a specific example, a detection of an erratic heartbeat or rhythm by a biometric sensor might cause the mobile device application to request information about the symptom "arrhythmia" and prompt the display of results having various conditions and ameliorative options for that symptom. An example of a supporting user interface is shown in FIG. 3C. Techniques for reading biometric sensors from a mobile device are supported by application frameworks such as the "e-Health Sensor Platform for Raspberry Pi."

In one embodiment, a user's medical history may be stored in DB 720. The user may enter the medical history directly through an interface 700 of the medical content search and ranking engine 710, or the user may select an option to interchange data with another health database storing the user's medical history. An example of a commercial medical history storage service that may allow data interchange is "MyMedicalRecords.com." A user's stored medical history may be used, in some cases, to assist in identifying relevant medical content related to the search term. A user's medical history may also provide information to the ranking engine to shape or inform the weights assigned to medical content references, provide additional filters, or provide relevant information for tie-breakers. For example, if it is known (via the stored medical history) that a user is allergic to painkillers containing codeine, then drugs containing codeine may not be presented as medical content in relation to a symptom or condition search. As an alternative example, if a user's medical history indicates that he or she has difficulty awakening from the anesthesia given for surgery, medical content for surgical procedures may be weighted lower than non-surgical treatment options, even when some surgical medical content may be weighted higher for patients not having difficulties with anesthesia.

Figure 9A:
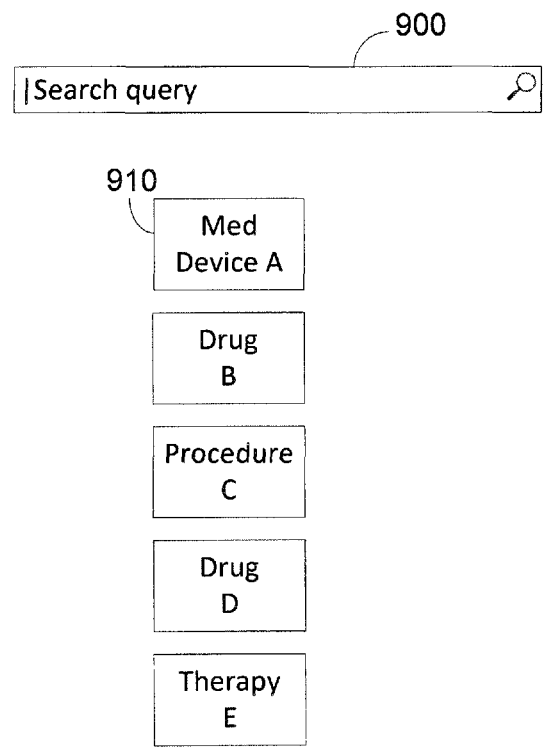
FIGS. 9A-9D illustrate example search result ordered list presentations.
Figure 9B:
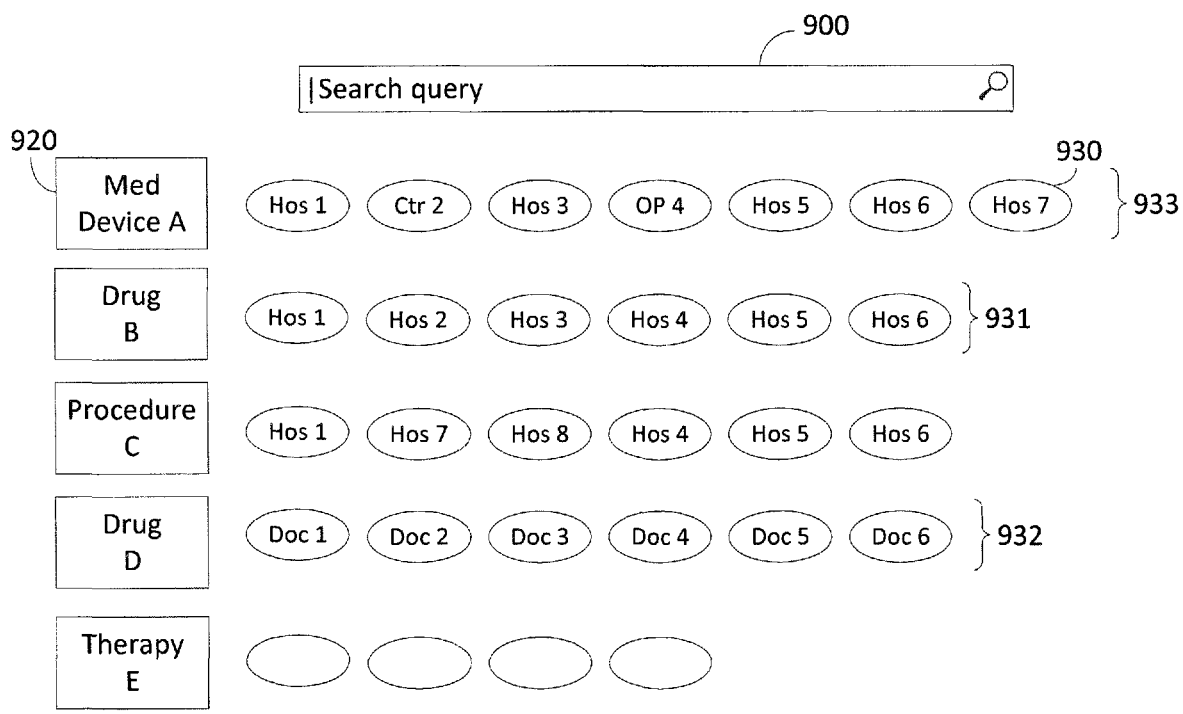

FIGS. 9A and 9B illustrate example search result ordered list presentations. Several kinds of medical content are exemplified in FIGS. 9A-9B, but should not be considered as limiting. In response to receiving a search query in the search input field 900 of a user interface, an ordered listing of medical content can be displayed. In FIG. 9A, the medical content 910 may be presented in a list from most referenced to least referenced. Additional filters (such as shown in FIG. 8) may be applied to further narrow the listing.

Results of the search can be presented with indicators of the number of providers that referenced the medical content, a specific indicator (e.g., a badge or icon) for each provider that references the content, an individual healthcare professional that references the content within a facility, a specific disease or symptom that the content is targeted toward, a demographic attribute, credentials of a healthcare provider, the level or severity of side effects that may be caused by the treatment option represented by the content, and/or other information that can support the ranking of the medical content (e.g., provide information regarding the relevancy) and/or provide additional information that a user may use to select an item of content or obtain additional information.

For example, referring to FIG. 9B, the medical content 920 may be presented with an indicator 930 of the providers that referenced the content. In one implementation using an indicator (e.g., icon or badge) for a particular medical facility provider that referenced an item of content, the indicator can be used once per content even if the content is referenced by multiple healthcare professionals at the facility 931. Thus, each indicator represents that a medical facility has referenced the content at least once. In another implementation, the indicator for a particular facility that referenced a content item may be used to represent each reference to the content so that multiple indicators for that particular facility may be shown for the referenced content when multiple healthcare professionals at that facility reference the content. In some cases, each indicator may show a healthcare professional's name or other information 932. In another implementation, a counter may be displayed on the healthcare provider indicator to indicate the number of times the content was referenced.

As described with respect to FIG. 8, results can be filtered. In one scenario, the results are filtered by provider or a select grouping of providers. For example, the results can be filtered to show rankings based on ranking services of top healthcare providers, by providers in a particular geographical locality, by a user-specified provider or providers, by a top number of providers in a specialty area (as ranked by a provider ranking system), by a type of provider, or by other provider-related configuration.

As illustrated in FIG. 9B, each item of medical content can include one or more indicators of the healthcare provider referencing the content. The indicators can be presented in order (e.g., left to right) of the provider's ranking on the U.S. News and World Report medical provider ranking system, Top 100 Hospitals Website, Hospital Webometrics, or other healthcare provider ranking system. Sometimes, healthcare providers may be of mixed type, for example showing indicators for hospitals, surgical centers, and outpatient facilities with respect to the same content 933. In some cases, whether indicators are shown in mixed mode may depend on the type of content (e.g., whether the content is a procedure, drug, device, therapy, etc.). In some embodiments, healthcare providers may be of a single type designated by the user in the search and filtering interface of FIG. 8. In some cases, individual healthcare professionals may be grouped together by their facility to create a single indicator badge. In some embodiments, the indicator badges may show the name (or other details) about a referencing healthcare professional. In some embodiments, selecting a healthcare facility indicator badge (e.g., a hospital) may cause additional interfaces to be rendered that display the individual healthcare professionals within the facility who prescribed, recommended, or used the medical content.

In some implementations, when multiple medical content (e.g., devices, drugs, procedures, therapies) within the results have a same number of providers that reference the content, the content having a same number of references may be presented in alphabetical order. In other implementations, the content may be presented in reverse chronological order, the results being weighted for recency of reference.

In some implementations, various mechanisms may be used to break ties between content that may have the same rankings (or are the same within a designated range). In some cases, the ranking order of tied results may be presented based on a ranking system of the healthcare providers that reference the content, such as the U.S. News and World Report. As noted, other ranking systems or sources may be used.

Another kind of tie-breaking mechanism that may be used to sort equally-ranked content is the content type (or subtype) of the medical content. For example, drugs may be prioritized above surgical procedures as preferential in some cases. Certain means of administration may be prioritized above other types, such as a preference for oils containing cannabis to dried-leaf forms.

Another type of tie-breaker that may be used refers to the credentials of the healthcare provider (medical facility or healthcare professional). For example, some healthcare professionals are board certified in particular specialties such as "internal medicine." Thus, ties may be effectively broken among content by considering the board certification/specialty status of healthcare professionals in comparison to the content referenced by individuals without board certification status. As a specific example, if a medical device and a drug are tied in the number of references received, but the drug received more prescriptions by board certified professionals, the drug may be ranked higher than the medical device.

Another type of tie-breaking mechanism may consider the incidence of side-effects caused by the medical content. Side-effect data may be stored in database 720 and accessed and analyzed by the medical content search and ranking engine 710. Among the side-effect data that may be stored in database 720 are the type, severity, and frequency of side-effects. Any or all of this side-effect data may be a factor in ranking a given item of medical content with respect to other medical content. For example, a tie between two items of medical content might be broken based a lower frequency of side effects in one content. An aspect of side-effect data may sometimes be a consequence related to the strength of the dosage of a substance; this might include not only higher dosages of typical pharmaceuticals, but also differing dosage properties of different types of botanical or herbal treatments (e.g., different variants of cannabis may have different strengths per mass unit).

It should also be noted that provider rankings and credentials, medical content type, and side-effect data as described with respect to tie-breaking mechanisms may also be used as weighting factors (as described above) to minimize or strengthen the numerical count of an individual reference.

In addition, one or more tie-breaking mechanisms may be applied to the listings of the results where a first tie breaking method does not break all the ties. As a non-limiting illustrative example, the ranking or credentials of the referencing provider may be first considered to break ties within the same ranked content. Any remaining ties may be broken by type of medical content or incidence of side-effects.

In some implementations, a user's option selection or user's medical history may be considered in choosing a tie-breaking mechanism. For example, if it is known via a user's medical history data stored in a DB 720 that the user has an allergy to a specific drug or substance, a "drug" medical content may be ranked lower than a surgical option. As another example, if a user has selected an option via a user interface 700 element to favor drug therapies over surgical options as medical content, a drug medical content may be shown above an equally-referenced surgical option.

Indicators may show other kinds of ranking criteria for medical content. Indicator types might include, for example, the type of reference (e.g., prescribed, recommended, used, purchased), healthcare professional name, specialty, board certification, geographic locality, and ranking organization (e.g., USNWR) indicators may be shown in some cases, depending on the criteria for ranking. In some cases, more than one indicator type may be shown, and the indicators may be grouped by type. Groups of badges may include, for example, groups for the medical facilities, healthcare professionals, and specialties referencing the content.

The user may sometimes desire to sort or filter results differently after the search results have been displayed in the search results list presentation. In some embodiments (not shown in FIG. 9B), user interface elements displaying additional filters can allow a user to group or select/deselect content types, provider types, reference types, or other filter criteria from the results on the search results list presentation.

Figure 9C:
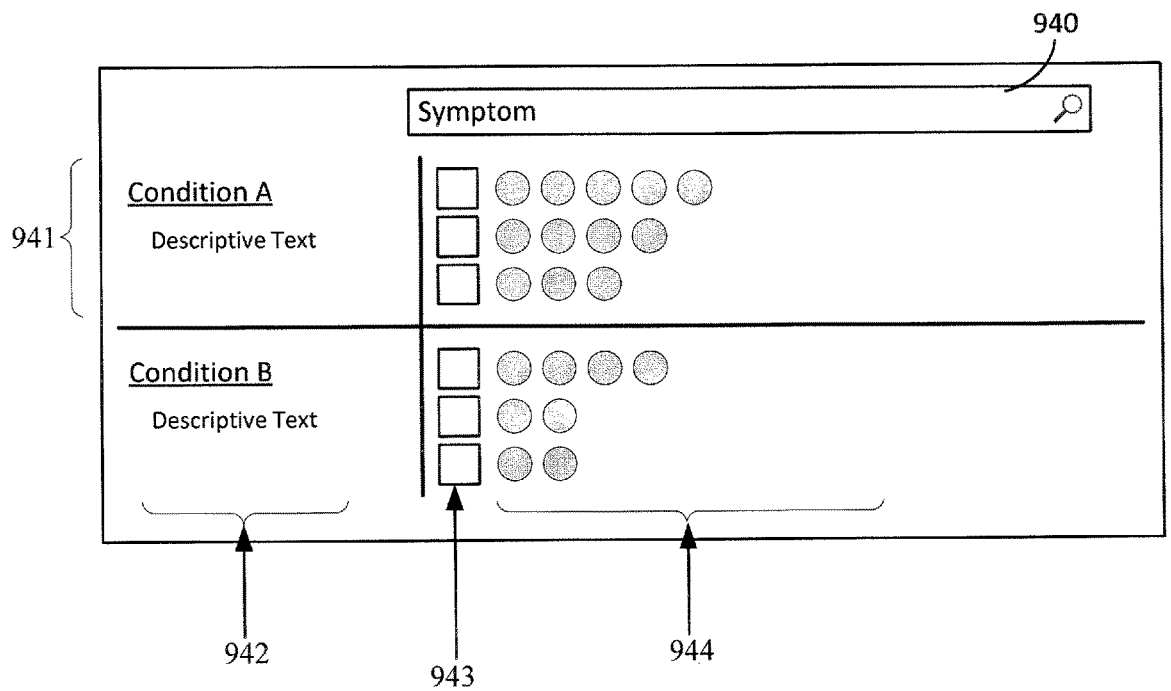

FIG. 9C shows an example ordered search result list presentation that may be used in some implementations. An interface is shown in FIG. 9C that may be appropriate for displaying search results for a designated symptom indicated by a search term, filter, or interpreted from a biometric sensor device. The interface in FIG. 9C shows search results grouped by condition first, and then by ordered content with indicator badges.

The conditions displayed may be selected and ordered by likelihood that the symptom search term relates to a given condition or disease. Information about a symptom's probability of relationship to a condition may be informed by accessing an existing medical diagnostic system (for example, the WebMD® "Symptom Checker"). A probability of association between a symptom and a condition may in some cases be informed by the reference counting data recorded by the medical content search and ranking system.

In the figure, the results for an example search of conditions and content related to a symptom 940 are shown. Content is grouped by condition 941, which may have such interface elements as a condition name and/or descriptive text 942. Conditions may in some cases be ordered by likelihood that the symptom relates to the condition. In another area of the interface, a list of content 943 may be presented for each condition 941 that is ordered in accordance with the techniques disclosed herein. Each content 943 may show a series of indicator badges 944 indicating information about the referencing provider (or other information).

Figure 9D:
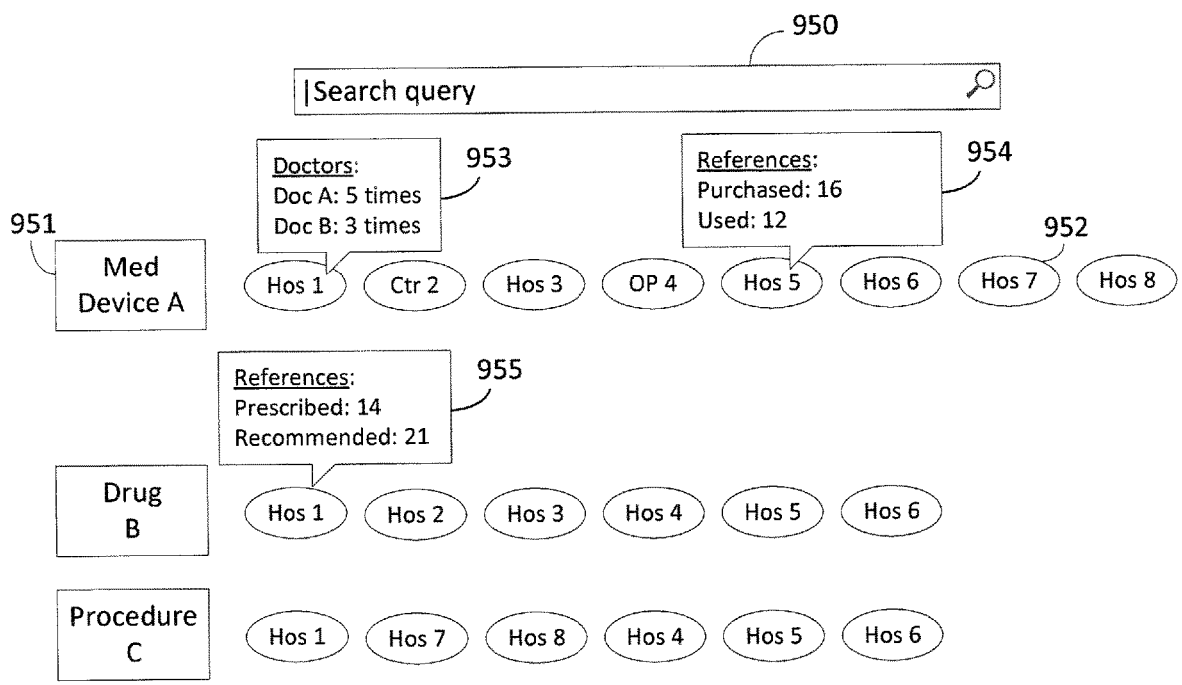

FIG. 9D illustrates an example ordered search result list presentation that may be used in some implementations. The example in FIG. 9D shows search query results of medical content with indicator badges and indicator popups. The search query 950 returns several search results of medical content 951. Each medical content result displays one or more indicator badges 952 of hospitals, doctors, or medical facilities.

Indicator popups (953, 954, 955) may show additional information about the selection criteria for an indicator badge, including such information as the individual doctors at a medical facility who referenced the medical content, or the number of references of a reference type. The indicator popups may show information that is appropriate or relevant both to the medical content type, the reference type, and the nature of the indicator badge. For example, in the figure, "Medical device A" was referenced by two individual doctors ("Doc A" and "Doc B") at "Hospital 1" for a total of 5 and 3 times, respectively 953. The indicator popup for "Hospital 5" 954 shows the information divided by reference type indicating the number of times the "Hospital 5" purchased and used "Medical Device A" 951. "Drug B" has a different indicator popup for "Hospital 1" 955, reflecting the nature of drug medical content, showing the number of times "Hospital 1" has prescribed and recommended the drug.

Naturally, other information may be displayed in indicator popups. For example, indicator popups may show condition or symptom information, side effect data, board certifications, specialties, provider rankings, or other information that may be used to understand the basis for ranking indicators or provide more detail to a user. The information in indicator popups will, of course, vary by the nature and type of indicator used shown in the results presentation. Use of the term "indicator popups" is not intended to be limiting of the type and manner of presenting additional information about an indicator. Many other types of interface elements are possible, as will be appreciated by practitioners in the art.

Mixed Content Types

An aggregation of information can be presented so that other search engines and databases, including those available through a search engine like Google™ and Bing®, can be performed and the results presented side-by-side together. In some cases, multiple types of searches (e.g., educational content searches, medical content searches, web search engines like GOOGLE and BING, video/audio content searches like available through YOUTUBE, and specific database searches) can be performed and presented simultaneously in a side-by-side arrangement. For example, if a user searches for the term "epilepsy," a search result presentation having varied content types, such as medical content, educational content, internet search results, internet video/audio, and television content may be desirable.

In some cases, the multi-type search can involve a universal query (e.g., a same query or terms and/or filtering applied to all search types being presented) and specific search query functionality associated directly with each search type. In this manner, various levels of granularity of searching may be applied. In some implementations, multiple types of content may be ranked and grouped within the respective content type and then presented together.

Figure 10:
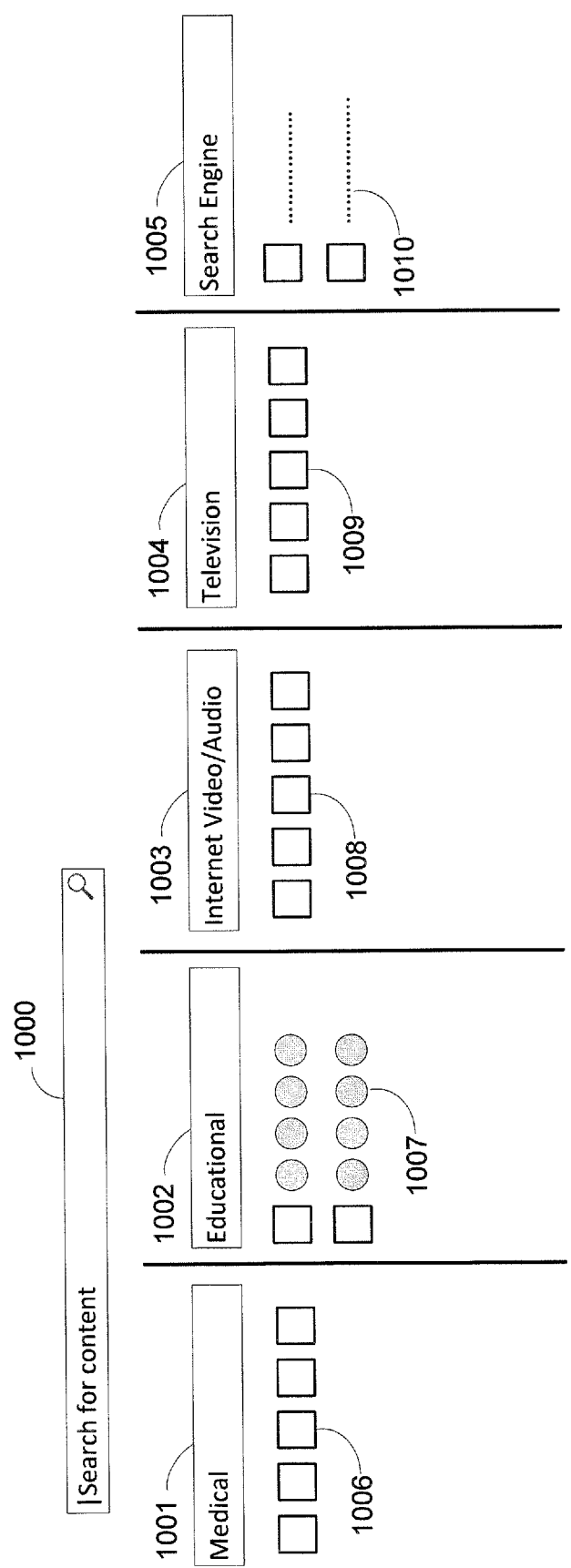
FIG. 10 shows an example search result presentation having multiple content types.

FIG. 10 shows an example search result presentation having multiple content types. In response to receiving a search query in the search input field 1000 of a user interface, an ordered listing of various types of content can be displayed. Medical content 1001 and educational content 1002 may be shown alongside internet audio/video 1003, television 1004, and search engine 1005 content. It should be noted that the types and categorizations for a search result presentation having multiple content types will be dependent on the nature and terms of the search query, as well as on user preferences which may be set using additional user interface elements (not shown).

Medical content 1001 may include results ordered or grouped in several ways, for example as shown in FIGS. 9A-9D. In the case of a search query for "epilepsy," for example, medical content may include therapies, procedures, and drugs (including medicinal use of cannabis as a therapy). Depending on the nature of the results, search results may be grouped or ordered 1006 by content type, sub-type, or other filter as described, for example by placing medical devices side by side with pharmaceuticals and medical procedures.

Educational content 1002 may include results presented in a variety of ways 1007, discussed with respect to FIGS. 3A-3E, 4, and 5. For example, indicators may present rankings information, indicator popups may show further information about sources, and content may be navigable with further navigation interfaces. In the case of a query for "epilepsy," for example, educational content may include textbooks, journal articles, or other content related to the topic.

In some cases, educational content may include internet audio/video content, as previously described; however, sometimes internet audio/video content may be grouped as its own content type 1003. Internet audio/video content 1003 may, of course, be further grouped and filtered 1008, for example by website (e.g., YouTube®, Coursera®), and/or by sub-type (e.g., lectures, entertainment, how-to). Additional navigation interfaces (not shown) for directing the user to specific content within an audio or video file, for example by transcribing a video and searching for terms within the transcription, may be provided in some cases. Navigation interfaces for videos were discussed with respect to 357 of FIG. 3D. In the case of a query for "epilepsy," for example, an internet audio/video search result might include a training video depicting the proper first aid procedure for a person having an epileptic seizure. Any and all educational content, including search bars to search specific content, may be presented side by side other content.

A single show can be traversed like a specific content match can be, wherein descending ranked previews for transcripts with matches and video/audio at the time of the match so when user hits play the video and transcript run simultaneously, although one or the other could be searched or traversed independently (e.g., search merely the transcript side by side leaving the video where it was/is, traverse the video by the matches therein but leave the transcript or preview in place). Both can be searched/traversed at once as to make the transcript always match the video/audio, even when traversing both or one or the other even, and even when playing the video/audio as to have the transcript thereto run with it while being next to it in the other of the side by sides.

Television content 1004 may be ranked according to techniques disclosed herein where referencing can include viewership. Television content 1004 may be filtered and/or grouped, such as by content type 1009 (e.g., news, documentary, drama) and origin (e.g., Bloomberg, CNN, CBS). In the case of a query for "epilepsy," for example, a TV search result might include a documentary on epilepsy research recently airing on an educational channel.

Viewership for TV could be determined for a specific second or for highest point in the TV program. Viewership for TV transcribed inventions (and/or internet video/audio inventions), can be done multiple ways: 1) each show or TV program can be used unlimited amounts of times for the ranking as to have every match be an independent content ranked and allow for a single show in the same hour to be ranked more than once in the ranking; 2) each show or program can be merely a single ranked content (for rankings, but queued at first to the highest ranked match for the content) only once for that particular show (next day or different particular show=new show that can be ranked too in same ranking depending on time filter) or episode 3) only allow a specific episode to be a single content in the ranking of all TV contents, but have the episode be queued to highest ranked match therein, and be traversed by the rank of matches. Controls for front to back may be present.

The inventions/ranking for internet video/audio ranking of video/audio can be used as a tie breaker for video with same amount of references (or vice versa). In some cases, video/audio rank based on viewership rank may be crossed with other rankings to alter the rankings. Also, in some embodiments, viewership may serve as a tiebreaker.

In some embodiments, additional content types may be shown. For example, traditional search engine results 1005 may be shown in some cases to display other relevant content 1010. In some cases the search engine results may be modified or grouped as appropriate.

Certain aspects may be made suitable for small form factors such as available through smartphones. In some embodiments for either within book search for matching words or a search for content in general, indicators may be omitted or represented in a different manner. For example, a link can be provided instead of a set of icons so that a user can select the link to see the source (or sources) that references the content. As another example that may be used in addition to or as an alternative to the link, a number, ratio or percentage can be provided adjacent the content title or description to indicate number of times the content is referenced (and provide a rank).

Certain aspects may be included that are suitable for large form factors. For example, large displays or projector screens may enable multiple results listings and previews. In addition, side-by-side views can be provided in a user interface to enable independent searching, filtering and/or types of results within a same view screen.

It should be noted that the described search and ranking engine may be accessible via a personal assistant such as Siri® available from Apple Inc., Google Now™, or Cortana® available from Microsoft Corp. Search Queries may be input through voice commands or by touch or text or other input.

Figure 11:
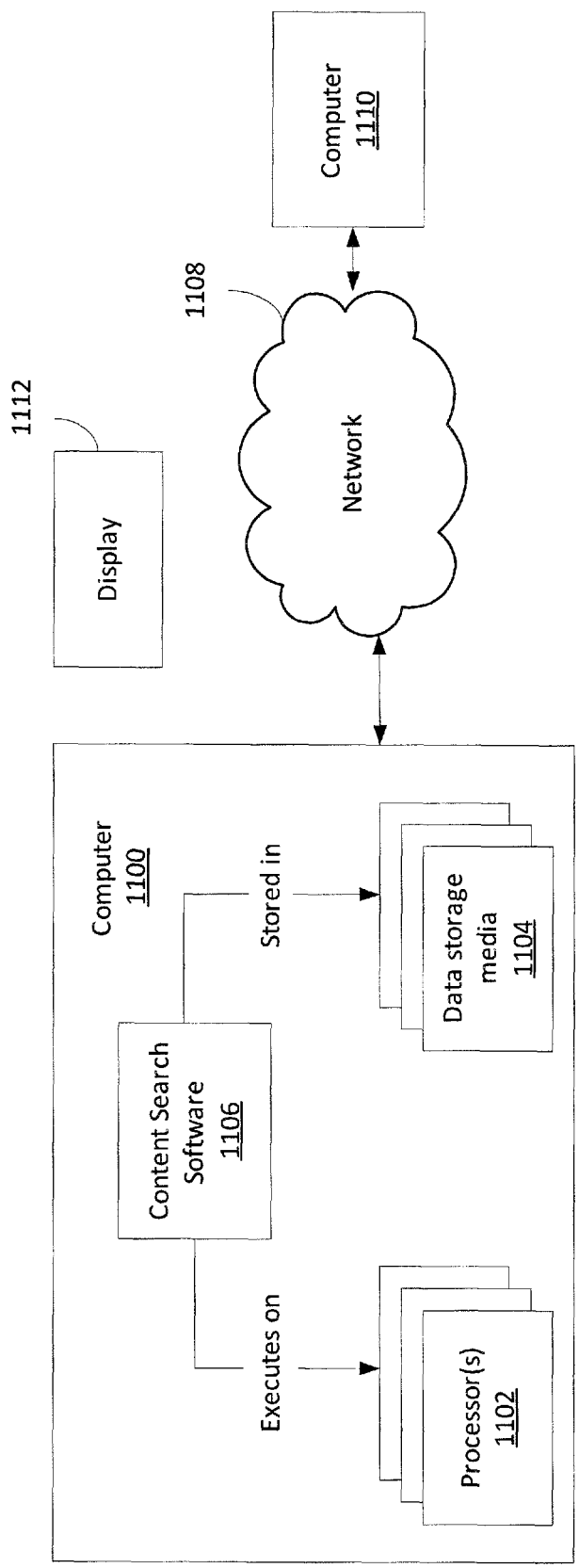
FIG. 11 is a block diagram of example components that may be used in connection with implementations of the subject matter described herein.

FIG. 11 shows an example environment in which aspects of the subject matter described herein may be deployed.

Computer 1100 includes one or more processors 1102 and one or more data storage media 1104. Processor(s) 1102 are typically microprocessors, such as those found in a personal desktop or laptop computer, smartphone, tablet, a server, a handheld computer, or another kind of computing device. Data storage media 1104 are components that are capable of storing data for either the short or long term. Examples of data storage media 1104 include, but are not limited to, hard disks, removable disks (including optical and magnetic disks), volatile and non-volatile random-access memory (RAM), read-only memory (ROM), flash memory, magnetic tape, and the like. The data storage media may also include other computer-readable storage media; however it should be understood that the data storage media and computer-readable storage media do not include propagating signals and carrier waves.

The computer 1100 may include, or be associated with, display 1112, which may be a cathode ray tube (CRT) monitor, a liquid crystal display (LCD) monitor, or any other type of monitor or display device.

Software may be stored in the data storage media 1104. The software can be executed by the one or more processor(s) 1102. An example of such software is content search software 1106, which may implement some or all of the functionality described herein, although any type of software could be used. Software 1106 may be implemented, for example, through one or more components, which may be components in a distributed system, separate files, separate functions, separate objects, separate lines of code, etc.

A computer (e.g., personal computer, server computer, handheld computer, smartphone, tablet) in which a program is stored on hard disk (or solid state drive or other storage media), loaded into RAM, and executed on the computer's processor(s) typifies the scenario depicted in FIG. 11, although the subject matter described herein is not limited to this example.

The subject matter described herein can be implemented as software that is stored in one or more of the data storage media 1104 (or computer-readable storage media) and that executes on one or more of the processor(s) 1102. The instructions to perform the acts could be stored on one medium, or could be spread out across plural media, so that the instructions might appear collectively on the one or more computer-readable storage media, regardless of whether all of the instructions happen to be on the same medium. It is noted that there is a distinction between media on which signals are "stored" (which may be referred to as "storage media"), and—in contradistinction—media that contain or transmit propagating signals. DVDs, flash memory, magnetic disks, etc., are examples of storage media. On the other hand, wires or fibers on which signals exist ephemerally are examples of transitory signal media. Thus, it will be understood that a storage media is non-transitory.

Additionally, any acts described herein (whether or not shown in a diagram) may be performed by a processor (e.g., one or more of processors 1102) as part of a method. Thus, if the acts A, B, and C are described herein, then a method may be performed that comprises the acts of A, B, and C. Moreover, if the acts of A, B, and C are described herein, then a method may be performed that comprises using a processor to perform the acts of A, B, and C. In one example environment, computer 1100 may be communicatively connected to one or more other devices through network 1108. Computer 1110, which may be similar in structure to computer 1100, is an example of a device that can be connected to computer 1100, although other types of devices may also be so connected.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

All patents, patent applications, provisional applications, and publications referred to or cited herein are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application.

What is claimed is:

1. A computer-based educational content search and results generation system, the system comprising: one or more non-transitory computer readable storage media; an educational content database stored on the one or more non-transitory computer readable storage media; and an educational content search and ranking engine that, when executed by one or more processors, directs the one or more processors to: identify a plurality of educational content from the educational content database in response to receiving a search query; identify a number of times each educational content of the plurality of educational content has been referenced by sources of a set of at least one designated source; generate a search result of the plurality of educational content that is in a ranked order based on the number of times each educational content has been referenced; and display the search result of the plurality of educational content, wherein the display of the search result comprises each respective educational content of the plurality of educational content having corresponding to it at least one respective source indicator for each respective source that referenced the respective educational content; wherein a plurality of source indicators correspond to a highest ranked educational content, and a plurality of source indicators correspond to a second highest ranked educational content; wherein each source has a maximum of only one source indicator for each educational content, even if a source has multiple references for an educational content; wherein at least one source indicator comprises a name of the respective source; wherein each educational content of the plurality of educational content is a book, textbook, or video; wherein the set of at least one designated source consists of schools, colleges, or universities; wherein the system is configured for a user to execute a search or filter for a particular degree; wherein the set of at least one designated source comprises at least one source that referenced at least one educational content of the plurality of educational content by assigning or requiring the educational content for a course; wherein the plurality of educational content is a respective plurality of educational content for a respective course corresponding to a respective degree, and wherein each educational content of the respective plurality of educational content was assigned or required for the respective course corresponding to the respective degree; wherein multiple courses for a respective degree each has a respective plurality of educational content displayed that is in a ranked order based on the number of times each educational content has been referenced, wherein each plurality of educational content comprises each respective educational content of the plurality of educational content having corresponding to it at least one respective source indicator for each respective source that referenced the respective educational content, and wherein each educational content of each respective plurality of educational content was assigned or required for the respective course corresponding to the respective degree; wherein the system is configured for at least one filter to be applied by the user through a tool bar, input field, menu, or other user interface element.

2. The system of claim 1, wherein at least one source indicator popup is configured to display.

3. The system of claim 1, wherein multiple source indicators each has a source indicator popup that is configured to display.

4. The system of claim 1, wherein at least one matched within-educational-content preview is configured to display.

5. The system of claim 1, wherein multiple educational contents each has a respective matched within-educational-content preview configured to display.

6. The system of claim 1, wherein identifying a plurality of educational content comprises executing a degree audit search or filter.

7. The system of claim 1, wherein identifying a plurality of educational content comprises using a degree audit search or filter to identify at least one educational content that a school referenced for a particular course corresponding to a degree.

8. The system of claim 1, wherein at least one user interface element provides for filtering by source, or filtering by time of references, or filtering by degree, or filtering by educational content type, or filtering by subject.

9. The system of claim 1, wherein the set of at least one designated source comprises a set designated by the user.

10. The system of claim 1, wherein a search term is altered by the search and ranking engine.

11. The system of claim 1, wherein each educational content for each plurality of educational content is referenced as part of a school's required curriculum.

12. The system of claim 1, wherein a Google, Bing, or other search engine result is also displayed.

13. The system of claim 1, wherein at least one source indicator popup is configured to display, wherein the source indicator popup is configured to display identifying information of one or more individuals who referenced the respective educational content.

14. The system of claim 13, wherein the source indicator popup is also configured to display an amount of references from any individual who is identified in the popup.

15. The system of claim 1, wherein at least one source indicator popup is configured to display, wherein the source indicator popup is configured to display multiple reference types.

16. The system of claim 15, wherein the source indicator popup is also configured to display an amount of references from the source for each of the displayed reference types.

17. The system of claim 1, wherein the user can select one or more educational contents from a plurality of educational content to be searched; wherein at least one matched within-educational-content preview is subsequently displayed; and wherein each educational content for each plurality of educational content is a textbook or book; and wherein a table of contents match enables one or more corresponding pages from the table of contents match to be used for one or more matched within-educational-content previews.

18. The system of claim 1, wherein a page graph is configured to display for each educational content of a plurality of educational content; and wherein at least one page graph is configured to show information about referenced pages of an educational content.

19. The system of claim 3, wherein the user can select one or more educational contents from a plurality of educational content to be searched, wherein at least one matched within-educational-content preview is configured to display while also displaying a user interface element that allows the user to traverse to a next or previous within-educational-content match, or to traverse to a next or previous within-educational-content match based on a page rank of matched pages; and wherein the system is configured to present one or more advertisements at designated times or according to an amount of educational content accessed by the user, wherein an advertiser selected when the advertisement is to be presented, how the advertisement is to be presented, who is to receive the advertisement, or for which specific educational content the advertisement is to be presented; wherein the advertisement presented is from an advertiser who won an auction to present an advertisement through the system; and wherein the set of at least one designated source comprises a set designated by the user.

20. The system of claim 9, wherein the user can filter by time of references.

21. The system of claim 9, wherein the user can filter by one or more educational content types.

22. The system of claim 9, wherein the user can filter by one or more educational content types; and wherein the user can filter by time of references.

23. The system of claim 9, wherein the user can filter by how educational content is referenced by using a user interface element to filter by one or more reference types; and wherein the user can filter by when educational content was referenced by using a user interface element to filter by time of references.

24. The system of claim 9, wherein the user can filter by one or more reference types.

25. The system of claim 1, wherein each educational content for each plurality of educational content is a book or textbook.

26. The system of claim 25, wherein the one or more processors are further directed to provide access to at least one educational content whereby at least one matched within-educational-content preview is displayed; and wherein providing access to the at least one educational content comprises presenting text of the educational content, and presenting one or more advertisements at one or more designated times or according to an amount of educational content accessed by the user.

27. The system of claim 23, wherein the user can filter by one or more educational content types.

28. The system of claim 1, wherein the user can select one or more educational contents from a plurality of educational content to be searched.

29. The system of claim 28, wherein at least one matched within-educational-content preview is configured to display.

30. The system of claim 29, wherein multiple within-educational-content previews are configured to display.

31. The system of claim 1, wherein multiple source indicators each has a respective source indicator popup that is configured to display; wherein at least one filter can be applied by the user through a tool bar, input field, menu, or other user interface element; wherein at least one user interface element provides for filtering by source, or filtering by time of references, or filtering by degree, or filtering by educational content type, or filtering by subject; and wherein the set of at least one designated source comprises a set designated by the user.

32. The system of claim 31, wherein at least one matched within-educational-content preview is configured to display.

33. The system of claim 31, wherein the one or more processors are further directed to provide access to at least one educational content whereby at least one matched within-educational-content preview is displayed; and wherein providing access to the at least one educational content comprises presenting text of the educational content, and presenting one or more advertisements at one or more designated times or according to an amount of educational content accessed by the user.

34. A computer-based educational content search and results generation system, the system comprising: one or more non-transitory computer readable storage media; an educational content database stored on the one or more non-transitory computer readable storage media; and an educational content search and ranking engine that, when executed by one or more processors, directs the one or more processors to: identify a plurality of educational content from the educational content database in response to receiving a search query; identify a number of times each educational content of the plurality of educational content has been referenced by sources of a set of at least one designated source; generate a search result of the plurality of educational content that is in a ranked order based on the number of times each educational content has been referenced; and display the search result of the plurality of educational content, wherein the display of the search result comprises each respective educational content of the plurality of educational content having corresponding to it at least one respective source indicator for each respective source that referenced the respective educational content; wherein each source has a maximum of only one source indicator for each educational content, even if a source has multiple references for an educational content; wherein at least one source indicator comprises a name of the respective source; wherein each educational content of the plurality of educational content is a book, textbook, or video; wherein the set of at least one designated source consists of schools, colleges, or universities; wherein the set of at least one designated source comprises at least one source that referenced at least one educational content of the plurality of educational content by assigning or requiring the educational content for a course; wherein the plurality of educational content is a respective plurality of educational content for a respective course corresponding to a respective degree, and wherein each educational content of the respective plurality of educational content was referenced for the respective course corresponding to the respective degree; wherein multiple courses for a respective degree each has a respective plurality of educational content displayed, and wherein each educational content of each respective plurality of educational content was referenced for the respective course corresponding to the respective degree; wherein multiple source indicators each has a respective source indicator popup that is configured to display;

wherein at least one filter can be applied by a user through a tool bar, input field, menu, or other user interface element; wherein at least one user interface element provides for filtering by source, or filtering by time of references, or filtering by degree, or filtering by educational content type, or filtering by subject; and wherein the set of at least one designated source comprises a set designated by the user.

35. A computer-based educational content search and results generation system, the system comprising: one or more non-transitory computer readable storage media; an educational content database stored on the one or more non-transitory computer readable storage media; and an educational content search and ranking engine that, when executed by one or more processors, directs the one or more processors to: identify a plurality of educational content from the educational content database in response to receiving a search query; identify a number of times each educational content of the plurality of educational content has been referenced by sources of a set of at least one designated source; generate a search result of the plurality of educational content that is in a ranked order based on the number of times each educational content has been referenced; and display the search result of the plurality of educational content, wherein the display of the search result comprises each respective educational content of the plurality of educational content having corresponding to it at least one respective source indicator for each respective source that referenced the respective educational content; wherein each source has a maximum of only one source indicator for each educational content, even if a source has multiple references for an educational content; wherein at least one source indicator comprises a name of the respective source; wherein at least one educational content of the plurality of educational content is a book, textbook, or video; wherein the set of at least one designated source comprises a school, college, or university; wherein the set of at least one designated source comprises at least one source that referenced at least one educational content of the plurality of educational content by assigning or requiring the educational content for a course; wherein the plurality of educational content is a respective plurality of educational content for a respective course corresponding to a respective degree; wherein each educational content of the respective plurality of educational content was referenced for the respective course corresponding to the respective degree; wherein the system is configured to allow a user to select one or more educational contents to be searched;

wherein the system is configured to display at least one matched within educational content preview; wherein multiple educational contents of the plurality of educational content each has a respective matched within-educational-content preview that is configured to display; wherein the user can execute a search or filter for a degree; and wherein each educational content of the plurality of educational content is a book or textbook.

36. The system of claim 35, wherein the system is configured to present one or more advertisements at one or more designated times or according to an amount of educational content accessed by the user; wherein multiple source indicators each has a respective source indicator popup that is configured to display; wherein the user can apply at least one filter through a tool bar, input field, menu, or other user interface element; wherein at least one user interface element provides for filtering by source, or filtering by time of references, or filtering by degree, or filtering by educational content type, or filtering by subject; wherein the set of at least one designated source comprises a set designated by the user; and wherein a user interface element is displayed that allows a user to traverse to a next or previous within-educational-content match, or to traverse to a next or previous within-educational-content match based on a page rank of matched pages; and wherein a table of contents match enables one or more corresponding pages from the table of contents match to be used for one or more matched within-educational-content previews.

37. The system of claim 19, wherein each educational content for each plurality of educational content is a textbook or book; and wherein a table of contents match enables one or more corresponding pages from the table of contents match to be used for one or more matched within-educational-content previews.

38. The system of claim 37, wherein a user interface element is configured to allow a user to select whether or not a table of contents match enables one or more corresponding pages from the table of contents match to be used for one or more matched within-educational-content previews.

39. The system of claim 1, wherein at least one source indicator popup is configured to display multiple class names of a respective source, and wherein another source indicator popup is configured to display multiple class names of a different respective source.

40. The system of claim 34, wherein at least one source indicator popup is configured to display multiple class names of a respective source, and wherein another source indicator popup is configured to display multiple class names of a different respective source.

41. The system of claim 35, wherein at least one source indicator popup is configured to display multiple class names of a respective source, and wherein another source indicator popup is configured to display multiple class names of a different respective source.

42. The system of claim 34, wherein a Google, Bing, or other search engine result is also displayed.

43. The system of claim 34, wherein each educational content for each plurality of educational content is a book or textbook; wherein the one or more processors are further directed to provide access to at least one educational content whereby at least one matched within-educational-content preview is displayed; and wherein providing access to the at least one educational content comprises presenting text of the educational content, and presenting one or more advertisements at one or more designated times or according to an amount of educational content accessed by the user; and wherein a table of contents match enables one or more corresponding pages from the table of contents match to be used for one or more matched within-educational-content previews.

* * * * *